US012797537B2

(12) United States Patent
Dugas

(10) Patent No.: US 12,797,537 B2
(45) Date of Patent: Nov. 17, 2026

(54) CAPACITIVE SENSING FOR DRUG DELIVERY

(71) Applicant: Analog Devices, Inc., Wilmington, MA (US)

(72) Inventor: Alan Dugas, Milton, MA (US)

(73) Assignee: Analog Devices, Inc., Wilmington, MA (US)

( * ) Notice: Subject to any disclaimer, the term of this patent is extended or adjusted under 35 U.S.C. 154(b) by 707 days.

(21) Appl. No.: 18/034,623

(22) PCT Filed: Mar. 11, 2021

(86) PCT No.: PCT/US2021/021801

§ 371 (c)(1),
(2) Date: Apr. 28, 2023

(87) PCT Pub. No.: WO2022/093306

PCT Pub. Date: May 5, 2022

(65) Prior Publication Data

US 2023/0398290 A1 Dec. 14, 2023

Related U.S. Application Data

(60) Provisional application No. 63/107,591, filed on Oct. 30, 2020.

(51) Int. Cl.
*A61M 5/168* (2006.01)
*A61M 5/145* (2006.01)

(52) U.S. Cl.
CPC ...... *A61M 5/16813* (2013.01); *A61M 5/1452* (2013.01); *A61M 5/16854* (2013.01);
(Continued)

(58) Field of Classification Search
CPC ............ A61M 2005/2006; A61M 5/20; A61M 2205/18; A61M 2205/3317;
(Continued)

(56) References Cited

U.S. PATENT DOCUMENTS

| | | | |
|---|---|---|---|
| 4,795,967 | A | 1/1989 | Fredericks |
| 5,304,347 | A | 4/1994 | Mann et al. |

(Continued)

FOREIGN PATENT DOCUMENTS

| | | | |
|---|---|---|---|
| EP | 2231203 | B1 | 2/2014 |
| EP | 3428585 | A1 | 1/2019 |

(Continued)

OTHER PUBLICATIONS

European Search Report received for Patent Application No. 21887080.6, mailed on Nov. 14, 2024, 16 pages.

(Continued)

*Primary Examiner* — Quynh-Nhu H. Vu
(74) *Attorney, Agent, or Firm* — ArentFox Schiff LLP

(57) ABSTRACT

Processes for using a capacitive sensor to control drug delivery are described. The capacitive sensor measures a capacitance across a pair of electrodes arranged along either side of a container. The container includes an air chamber, a fluid chamber, and a stopper separating the air chamber from the fluid chamber. A volume of drug in the fluid chamber may be determined based on the measured capacitance. The volume is compared to a target volume, and if the volume in the fluid chamber is greater than the target volume, a stopper actuator expels a portion of the drug from the fluid chamber.

28 Claims, 9 Drawing Sheets

(52) U.S. Cl.
CPC ............. *A61M 2005/16863* (2013.01); *A61M 2205/15* (2013.01); *A61M 2205/18* (2013.01); *A61M 2205/3327* (2013.01); *A61M 2205/3368* (2013.01); *A61M 2205/3379* (2013.01); *A61M 2205/60* (2013.01)

(58) Field of Classification Search
CPC ............. A61M 2205/3327; A61M 2205/3331; A61M 2205/3368; A61M 2205/3379; A61M 2205/3389; A61M 2205/50; A61M 5/1452; A61M 5/16813; A61M 5/1684; A61M 5/172; A61M 5/31576; A61M 5/16854
See application file for complete search history.

(56) References Cited

U.S. PATENT DOCUMENTS

| | | | | |
|---|---|---|---|---|
| 6,073,488 | A | 6/2000 | Byatt et al. | |
| 6,110,148 | A | 8/2000 | Brown et al. | |
| 6,316,864 | B1 | 11/2001 | Ormerod | |
| 6,352,523 | B1 * | 3/2002 | Brown | A61M 5/31546 222/23 |
| 6,542,350 | B1 * | 4/2003 | Rogers | A61M 5/14593 361/278 |
| 2005/0072228 | A1 | 4/2005 | Jakoby et al. | |
| 2007/0234796 | A1 | 10/2007 | Tshishiku | |
| 2007/0250005 | A1 * | 10/2007 | Fago | A61M 5/31525 604/113 |
| 2009/0069756 | A1 * | 3/2009 | Larsen | A61M 5/1782 604/246 |
| 2011/0314907 | A1 | 12/2011 | Wiedekind-Klein | |
| 2013/0286064 | A1 | 10/2013 | Muyskens et al. | |
| 2014/0142537 | A1 * | 5/2014 | Gibson | A61M 5/14546 604/67 |
| 2015/0045727 | A1 * | 2/2015 | Bammer | A61M 5/1684 73/304 C |
| 2015/0268656 | A1 * | 9/2015 | Bammer | G01F 23/266 700/231 |
| 2018/0093042 | A1 | 4/2018 | Klemm et al. | |
| 2019/0060577 | A1 | 2/2019 | Vallis | |
| 2020/0045162 | A1 * | 2/2020 | Novet | H04M 1/72454 |
| 2020/0129701 | A1 | 4/2020 | Dellimore et al. | |
| 2021/0186365 | A1 | 6/2021 | Kinio et al. | |

FOREIGN PATENT DOCUMENTS

| | | | |
|---|---|---|---|
| EP | 3594638 | A1 | 1/2020 |
| JP | 2019-174226 | A | 10/2019 |
| KR | 10-2007-0080816 | A | 8/2007 |
| WO | 99/30117 | A1 | 6/1999 |
| WO | 2007/107558 | A2 | 9/2007 |
| WO | 2014/166479 | A2 | 10/2014 |
| WO | 2017/021226 | A1 | 2/2017 |
| WO | 2019/121617 | A1 | 6/2019 |
| WO | 2021/183704 | A2 | 9/2021 |

OTHER PUBLICATIONS

International Search Report and Written Opinion issued in International Patent Application No. PCT/US2021/021801 on May 27, 2021.

Partial Supplementary European Search Report issued in European Patent Application No. 21887080.6, dated Jul. 30, 2024 (14 pages).

European Search Report issued in European Patent Application No. 21767535 on Mar. 14, 2024, 9 pages.

International Search Report and Written Opinion received for PCT Patent Application No. PCT/US2021/021800, mailed on Sep. 27, 2021, 13 pages.

* cited by examiner

CAPACITIVE SENSING FOR DRUG DELIVERY

PRIORITY DATA

This application is a 35 U.S.C. § 371 National Stage Application of International Patent Application No. PCT/US2021/021801, filed Mar. 11, 2021, which application claims the benefit of and priority to U.S. provisional patent application No. 63/107,591, filed Oct. 30, 2020, each of which applications is hereby incorporated herein by reference in its entirety.

TECHNICAL FIELD OF THE DISCLOSURE

The present invention relates to the field of capacitive sensing, in particular to methods for using capacitive sensing to measure contents of a container, such as a syringe used in a drug delivery system.

BACKGROUND

In some automated drug delivery systems, a drive system automatically pushes a plunger of a syringe containing a drug to push the drug out of the syringe. Current methods for monitoring the amount of the drug that has been delivered and/or the amount of drug remaining in the syringe involve using an electro-mechanical gearing system paired with an encoder to monitor the rotation of the drive shaft that pushes the plunger; the inferred stopper movement is used to estimate the stopper position, which is used to calculate volume of the drug remaining. This is an indirect measurement of the drug delivered, and it is subject to manufacturing issues and mechanical failures. For example, failures or breakdowns of the mechanical links between the motor, plunger rod, and stopper can affect measurements, as can shifts in motor rotations and gearing tolerances during manufacturing or after repeated usage of the delivery system.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Figure 1:
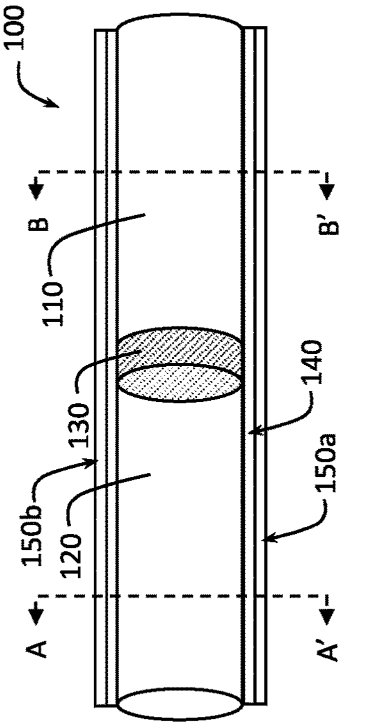
FIG. 1 is a side view of a cylindrical container having a capacitive sensor, according to some embodiments of the present disclosure.

The systems, methods and devices of this disclosure each have several innovative aspects, no single one of which is solely responsible for all of the desirable attributes disclosed herein. Details of one or more implementations of the subject matter described in this specification are set forth in the description below and the accompanying drawings.

A capacitive measurement system directly measures the amount of a fluid, such as a drug, within a container. As used herein, a drug may be any substance suitable for administration to a patient, such as a biopharmaceutical, synthesized pharmaceutical, blood or blood product, saline, etc. The container may be a container for delivering a drug, such as a syringe (e.g., a hypodermic syringe, oral syringe, intraosseous syringe, etc.), a component of an intravenous pump system, or a container for storing or transporting a drug, such as a vessel or vial. In some embodiments, the capacitive measurement system may be used in non-medical applications, such as veterinary or lab applications.

The capacitive sensor includes two electrodes, such as electrode strips, positioned along the container. The electrodes extend lengthwise along an outer wall of a syringe and are positioned along opposite sides of the syringe, forming a capacitor around the syringe. The capacitance between the two electrodes varies based on the amount of drug in the container, so the capacitance measurement directly correlates to the amount of drug in the container. In general, a liquid drug has a significantly higher relative permittivity than air. In an example where a syringe is used to deliver a drug, as the stopper pushes the drug out of the syringe and air displaces the volume of the expelled drug, the measured capacitance across the syringe decreases. In an example where a container (e.g., a syringe or vial) is filled with a drug, as the volume of the drug in the container increases, the measured capacitance across the container increases.

In the syringe example, a syringe with electrodes extending along its outer walls can be modeled as a set of three capacitors connected in parallel: a first capacitor that includes an air chamber, a second capacitor that includes the stopper, and a third capacitor that includes a fluid chamber holding a drug. The total capacitance across the sensor is the sum of each of these capacitors' capacitances. Each of the air chamber, stopper, and fluid chamber capacitors comprises a series of dielectric layers, which can be modeled as capacitors connected in series.

For a particular sensor and container structure, the relationship between a capacitance measurement obtained by the sensor and the volume of biologic in the syringe can be obtained. Capacitance is related to the relative permittivities of the dielectrics and the thickness of the dielectrics, which are known, and the area of the electrode plates surrounding each of the parallel capacitor regions (i.e., the air chamber, fluid chamber, and stopper regions), which changes as the stopper is moved. The length of the fluid chamber ($L_{FC}$) is related to the volume of drug remaining in the chamber, e.g., the volume of the biologic is equal to $L_{FC}*\pi*r_{syringe}^2$ for a cylindrical syringe, where $r_{syringe}$ is the internal radius of the syringe. Thus, the capacitance measurement can be used to determine the volume of drug in the fluid chamber.

The capacitance measurement across a syringe or other container can be used for various applications. The capacitance measurement may be used by a drug delivery system to control delivery of a drug dose to a patient. The capacitance measurement may also be used to perform various fault detection checks, such as detecting leakage, occlusions, or drug fouling. In some examples, the capacitance measurement is used in combination with measurements of the environment of the drug delivery system, such as temperature and humidity, which affect relative permittivity. In some examples, a drug delivery system further includes pressure and/or power sensors to detect pressure in the fluid chamber and power supplied to the stopper actuator. Pressure and power measurements may help detect and identify leaks or occlusions. In another embodiment, capacitance measurements are used to control filling a container to a specified volume.

Embodiments of the present disclosure provide a method for monitoring delivery of a drug. The method includes measuring a capacitance across a pair of electrodes, the pair of electrodes arranged along either side of a container, the container comprising an air chamber, a fluid chamber, and a stopper separating the air chamber from the fluid chamber; determining, based on the measured capacitance, a volume of a drug in the fluid chamber; comparing the volume of the drug in the fluid chamber to a target volume; and in response to the volume of the drug in the fluid chamber being greater than the target volume, instructing a stopper actuator to expel at least a portion of the drug from the fluid chamber.

Further embodiments of the present disclosure provide method for delivering a drug that includes determining a target capacitance for a drug dose; measuring a capacitance across a pair of electrodes, the pair of electrodes arranged along either side of a container, the container comprising an air chamber, a fluid chamber, and a stopper separating the air chamber from the fluid chamber; comparing the measured capacitance to the target capacitance; and in response to the measured capacitance being greater than the target capacitance, instructing a stopper actuator to expel at least a portion of the drug from the fluid chamber.

Additional embodiments of the present disclosure provide a method for characterizing a drug that includes measuring a capacitance across a pair of electrodes, the pair of electrodes arranged along either side of a container, the container containing a drug; determining an expected capacitance across the pair of electrodes, the expected capacitance based on an expected volume of the drug in the container and an expected relative permittivity of the drug; comparing the measured capacitance to the expected capacitance; and in response to the measured capacitance being outside a tolerance threshold of the expected capacitance, outputting an alert.

Still other embodiments of the present disclosure provide a drug delivery system that includes a syringe holder, a stopper actuator couplable to the stopper, a measurement circuit, and a processor. The syringe holder holds a syringe containing a drug for delivery to a patient, the syringe comprising an air chamber, a fluid chamber, and a stopper separating the air chamber from the fluid chamber. The measurement circuit measures a capacitance across a pair of electrodes arranged along either side of the container. The processor receives a measured capacitance from the measurement circuit; determines, based on the measured capacitance, a volume of the drug in the fluid chamber; compares the volume of the drug in the fluid chamber to a target volume; and in response to the volume of the drug in the fluid chamber being greater than the target volume, instructs the stopper actuator to expel at least a portion of the drug from the fluid chamber.

Further embodiments of the present disclosure provide a drug delivery system that includes a syringe holder, a stopper actuator couplable to the stopper, a measurement circuit, and a processor. The syringe holder holds a syringe containing a drug for delivery to a patient, the syringe comprising an air chamber, a fluid chamber, and a stopper separating the air chamber from the fluid chamber. The measurement circuit measures a capacitance across a pair of electrodes arranged along either side of the container. The processor determines a target capacitance for a drug dose; receives a measured capacitance from the measurement circuit; compares the measured capacitance to the target capacitance; and in response to the measured capacitance being greater than the target capacitance, instructs the stopper actuator to expel at least a portion of the drug from the fluid chamber.

As will be appreciated by one skilled in the art, aspects of the present disclosure, in particular aspects of a using capacitive sensing to measure the contents of a container, and control algorithms based on capacitive sensing, described herein, may be embodied in various manners (e.g., as a method, a system, a computer program product, or a computer-readable storage medium). Accordingly, aspects of the present disclosure may take the form of a hardware embodiment, a software embodiment (including firmware, resident software, micro-code, etc.), or an embodiment combining software and hardware aspects that may all generally be referred to herein as a "circuit," "module" or "system." Functions described in this disclosure may be implemented as an algorithm executed by one or more hardware processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer-readable medium(s), preferably non-transitory, having computer-readable program code embodied, e.g., stored, thereon. In various embodiments, such a computer program may, for example, be downloaded (updated) to the existing devices and systems (e.g. to the existing perception system devices and/or their controllers, etc.) or be stored upon manufacturing of these devices and systems.

The following detailed description presents various descriptions of specific certain embodiments. However, the innovations described herein can be embodied in a multitude of different ways, for example, as defined and covered by the claims and/or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as “above”, “below”, “upper”, “lower”, “top”, “bottom”, or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase “between X and Y” represents a range that includes X and Y.

Other features and advantages of the disclosure will be apparent from the following description and the claims.

Capacitive Sensor Overview

Figure 2:
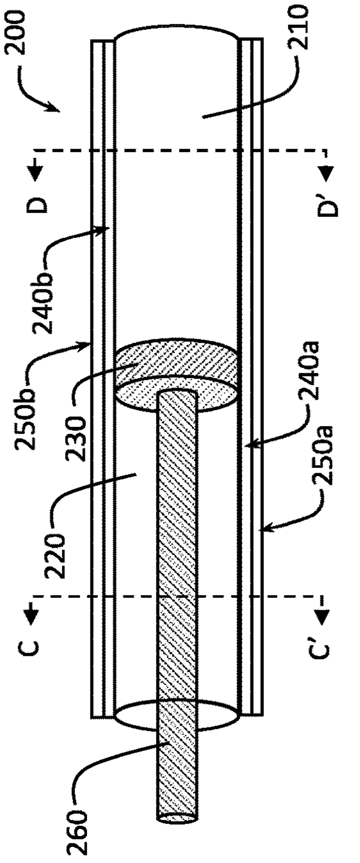
FIG. 2 is a side view of a syringe having a capacitive sensor, according to some embodiments of the present disclosure.

FIG. 1 is a side view of a cylindrical container having a capacitive sensor, according to some embodiments of the present disclosure. The container 100 has two interior chambers 110 and 120, which are separated from each other by a stopper 130. For example, the container 100 is a syringe, and one of the chambers 110, referred to as a fluid chamber 110, holds a drug or other substance for delivery to a patient. The other chamber 120 is an air chamber. In the orientation shown in FIG. 1, the stopper 130 moves towards the right to eject the contents of the fluid chamber 110, e.g., through a needle (not shown) attached to the syringe. The stopper 130 may be connected to a plunger rod, as shown in FIG. 2, that controls the position of the stopper 130. Alternatively, the position of the stopper 130 may be controlled by air pressure in the air chamber 120 or another mechanism.

The chambers 110 and 120 are enclosed by a wall 140, which may be glass, plastic, or another material. An inner side of the wall 140, referred to as an inner wall, is in contact with the chambers 110 and 120 and the stopper 130. A pair of electrodes 150 extend along an outer side of the wall 140, referred to as an outer wall. Alternatively, the electrodes 150 may extend along an inner side of the wall 140, referred to as the inner wall, or the electrodes 150 may be arranged within the walls 140 of the container. The electrodes 150 are on opposite sides of the wall 140; in the orientation shown in FIG. 1, one electrode 150*a* is along the bottom of the container 100, and the other electrode 150*b* is along the top of the container 100. In alternate embodiments, the container 100 includes a single chamber and no stopper 130 (e.g., the container 100 is a vial for holding a substance).

The electrodes 150 create an electric field within the container 100. The contents of the container 100 (i.e., the contents of the chambers 110 and 120 and the stopper 130) and the wall 140 are dielectric materials between the electrodes 150. These dielectric materials and the electrodes 150 form a capacitor. Capacitance varies based on the permittivity of dielectric material between the electrodes. If the stopper 130 moves left to right through the container 100, e.g., to push a drug out of a syringe, the volume of material in the fluid chamber 110 decreases while the volume of material in the air chamber 120 increases. In particular, if the stopper 130 pushes a drug out of a syringe, the amount of drug in the fluid chamber 110, and its volume is replaced with air in the air chamber 120. If the contents of the two chambers 110 and 120 have different permittivities, the measured capacitance corresponds to a change in the relative volumes of the two chambers 110 and 120. Typically drugs have a higher permittivity than air, so the measured capacitance decreases as the drug is pushed out of the container 100 and the volume of air between the electrodes 150 increases.

Figure 3:
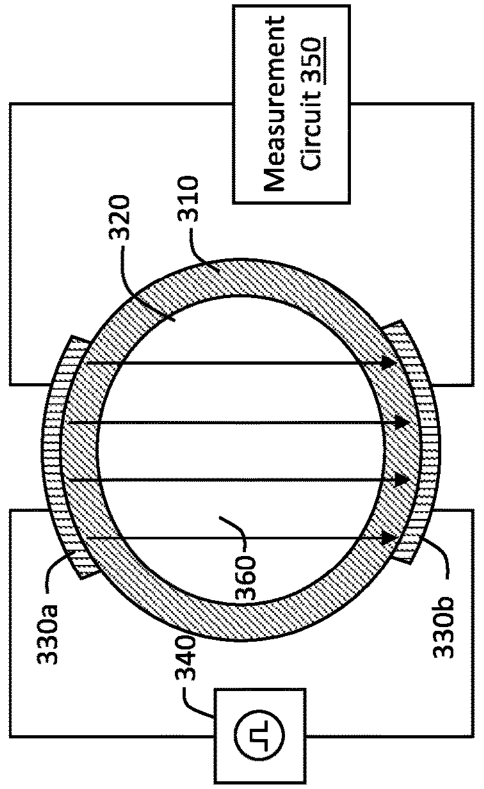
FIG. 3 is a cross-section of a portion of a container with a capacitive sensor, according to some embodiments of the present disclosure.

Two cross-sections, A-A' and B-B', are noted in FIG. 1. These two cross-sections, located on different sides of the stopper 130, may be similar but for the different contents of the chambers. In particular, the two cross-sections A-A' and B-B' have the same structure, but during use of the container 100, the two chambers 110 and 120 may be filled with different materials having different permittivities, e.g., chamber 110 is filled with air and chamber 120 is filled with a drug. FIG. 3, discussed below, represents an example of the cross-sections A-A' and B-B'.

FIG. 2 is a side view of a syringe 200 having a capacitive sensor, according to some embodiments of the present disclosure. The syringe 200 includes a fluid chamber 210, similar to the fluid chamber 110 in FIG. 1, for holding a drug or other substance. The syringe 200 includes an air chamber 220, similar to the air chamber 120 in FIG. 1. A stopper 230, similar to the stopper 130 in FIG. 1, separates the two chambers 210 and 220. A plunger rod 260 is coupled to the stopper 230 to control the position of the stopper 230. A needle or other outlet (not shown in FIG. 2) may be on the right side of the fluid chamber 210, opposite the stopper 230. When the plunger rod 260 pushes the stopper 230 towards the right, the stopper 230 expels material from the fluid chamber 210 and through the needle or other outlet.

The syringe 200 further includes a wall 240, which is similar to the wall 140, and electrodes 250 along an outer side of the wall 240. In the embodiment shown in FIG. 2, the syringe 200 includes two electrodes 250*a* and 250*b* along the outer wall, similar to the electrodes 150*a* and 150*b* shown in FIG. 1. As noted with respect to FIG. 1, in other embodiments the electrodes 250 may extend along an inner side of the wall 240, or the electrodes 250 may be arranged within the walls 240 of the container. In some embodiments, the stopper 230 and/or plunger rod 260 includes an electrode, e.g., the plunger rod 260 is a conductive material that forms an electrode, or the stopper 230 is wrapped by a conductive material that forms an electrode. A plunger rod or stopper electrode is referred to as an inner electrode, e.g., an electrode inside the syringe 200, and the electrodes 250 are referred to as an outer electrode, e.g., electrodes external to the syringe 200. In some embodiments, the syringe 200 includes two outer electrodes and an inner electrode. In some embodiments, the syringe 200 includes one outer electrode and an inner electrode.

Figure 4:
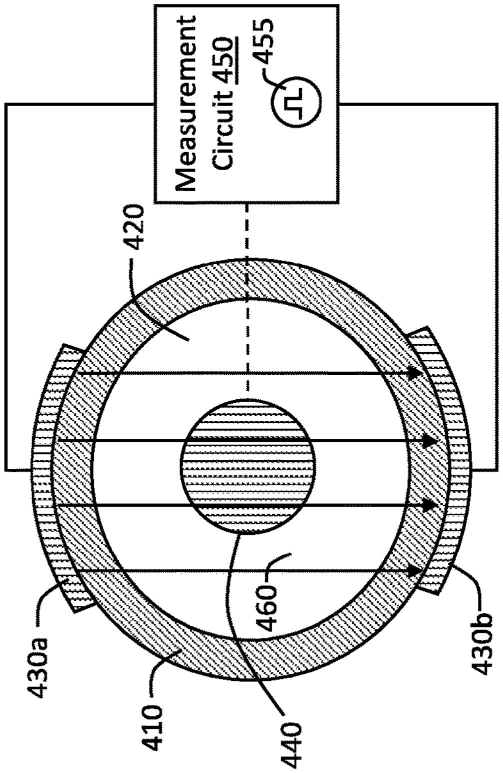
FIG. 4 is a cross-section of a portion of a syringe with a capacitive sensor, according to some embodiments of the present disclosure.

Two cross-sections, C-C' and D-D', are noted in FIG. 2. An example of the cross-section C-C', which includes the plunger rod 260, is shown in FIG. 4, discussed below. An example of the cross-section D-D', which does not include the plunger rod 260, is shown in FIG. 3.

FIG. 3 is a cross-section of a portion of a container with a capacitive sensor, according to some embodiments of the present disclosure. The cross-section includes a container wall 310, which may correspond to the wall 140 or 240. The wall 310 surrounds a chamber 320, which may correspond to any of the chambers 110, 120, or 210 discussed above. On the outside of the wall 310 are two electrodes 330*a* and 330*b*. The electrodes 330*a* and 330*b* are positioned on opposite sides of the wall 310. The electrodes 330*a* and 330*b* may be physically attached to the wall 310. For example, the electrodes 330*a* and 330*b* may be metal strips that are pasted or 3D printed to the wall 310. The electrodes 330*a* and 330*b* may have electrical connections configured to connect to a drug delivery monitoring system, e.g., wires or conductive patches. Alternatively, the electrodes 330*a* and 330*b* may be incorporated into a drug delivery device that can hold and dispense drugs from the syringe 200, or other another type of device for holding the container 100. When the container 100 or syringe 200 is loaded into the device, the electrodes 330*a* and 330*b* are positioned relative to the container 100 or syringe 200 as illustrated in FIGS. 1-4. In the embodiment shown in FIG. 2, if the plunger rod 260 and/or stopper 230 include an electrode, one of the electrodes 330*a* or 330*b* may be removed and only one electrode 330 is along the outer wall; this embodiment is described further with respect to FIGS. 4 and 9.

The electrodes 330*a* and 330*b* are electrically coupled to a voltage source 340. The voltage source 340 generates a voltage signal that is applied across the electrodes 330*a* and 330*b*. The voltage signal creates an electric field 360 between the electrodes 330*a* and 330*b*. The electric field 360 extends across at least a portion of the chamber 320. In this example, the voltage source 340 is a square wave source that generates a square wave voltage signal that is applied across the electrodes 330*a* and 330*b*. In other examples, other voltage stimulus signals, such as a sinusoidal or triangle voltage wave, may be used. The voltage signal may be a periodic signal with a fixed amplitude and frequency. Alternatively, the amplitude and/or frequency of the voltage signal may vary, e.g., based on instructions from a processor connected to the voltage source 340. While the electric field 360 is depicted by electric field lines that span from electrode 330*a* to 330*b*, it should be understood that the direction of the electric field may change based on the voltage signal applied by the voltage source 340.

The electrodes 330*a* and 330*b* are also electrically coupled to a measurement circuit 350. The measurement circuit 350 measures a capacitance across the electrodes 330*a* and 330*b*. Different contents of the chamber 320 have different permittivities, which affect the electric field 360 between the electrodes 330*a* and 330*b*. The capacitance measurement captured by the measurement circuit 350 reflects the contents of the chamber 320. In some embodiments, the measurement circuit 350 and voltage source 340 are incorporated on a single chip or device.

FIG. 4 is a cross-section of a portion of a syringe with a capacitive sensor, according to some embodiments of the present disclosure. The cross-section includes a container wall 410, which corresponds to the wall 240. The wall 410 surrounds a chamber 420, which corresponds to the air chamber 220 in FIG. 2. On the outside of the wall 410 is a first outer electrode 430*a*. In some embodiments, a second outer electrode 430*b* (shown with a dashed line) may be arranged on an opposite side of the wall 410 from the first outer electrode 430*a*. The electrodes 430*a* and 430*b* are similar to the electrodes 330*a* and 330*b* described with respect to FIG. 3. A plunger rod 440 within the chamber 420 corresponds to the plunger rod 260 shown in FIG. 2. The plunger rod 440 is an inner electrode that can form a capacitor with the first outer electrode 430*a*. The plunger rod 440 is located within the inner side of the wall 410. In embodiments with the second outer electrode 430*b*, the plunger rod 440 can also form a capacitor with the second outer electrode 430*b*. For example, a voltage source 455 can apply a voltage difference between the plunger rod 440 and the first outer electrode 430*a*, or between the plunger rod 440 and the second outer electrode 430*b*.

The outer electrodes 430*a* and 430*b* and plunger rod 440 are electrically coupled to a measurement circuit 450, which in this example includes a voltage source 455. The voltage source 455 is similar to the voltage source 340, and the measurement circuit 450 is similar to the measurement circuit 350. In this example, an electric field 460 extends between the first outer electrode 430*a* and the plunger rod 440. The electric field 460 extends across a portion of the chamber 420, as illustrated in FIG. 4.

Capacitor Model for a Syringe

Containers such as those shown in FIGS. 1-4 may be modeled as a set of capacitors connected in series and parallel. For example, the syringe 200 shown in FIG. 2 is modeled as a set of three capacitors connected in parallel: a first capacitor that includes the air chamber 220 and the plunger rod 260, a second capacitor that includes the stopper 230, and a third capacitor that includes the fluid chamber 210 holding a drug. The total capacitance across the capacitive sensor is the sum of each of these capacitors connected in parallel. Each of the air chamber, stopper, and fluid chamber capacitors comprises a series of dielectric layers, which can be modeled as capacitors connected in series. The fluid chamber capacitor has three dielectric layers between the electrodes 250: a first layer of the wall 240*a* (e.g., glass or plastic), a layer of drug in the fluid chamber 210, and a second layer of the wall 240*b*. The air chamber capacitor has a first layer of the wall 240*a*, a first air layer, the plunger rod 260, a second air layer, and a second layer of the wall 240*b*. The stopper capacitor has a first layer of the wall 240*a*, a layer of the stopper 230, and a second layer of the wall 240*b*. The capacitance of a given chamber is the inverse of the sum of the inverse of each layer's capacitance. Formulas (1)-(3) show the inverse capacitances of the fluid chamber capacitor ($C_{FC}$), the air chamber capacitor ($C_{AC}$) and the stopper capacitor ($C_{SC}$) as a function of the capacitances of the glass wall 240 ($C_{Glass}$), the drug in the fluid chamber 210 ($C_{Drug}$), the stopper 230 ($C_{Stpr}$), and the air in the air chamber 220 ($C_{Air}$):

$$\frac{1}{C_{FC}} = \frac{1}{C_{Glass}} + \frac{1}{C_{Drug}} + \frac{1}{C_{Glass}} = \frac{1}{C_{Drug}} + \frac{2}{C_{Glass}} = \frac{C_{Glass} + 2 * C_{Drug}}{C_{Glass} * C_{Drug}} \quad (1)$$

$$\frac{1}{C_{AC}} = \frac{1}{C_{Glass}} + \frac{1}{C_{Air}} + \frac{1}{C_{Glass}} = \frac{1}{C_{Air}} + \frac{2}{C_{Glass}} = \frac{C_{Glass} + 2 * C_{Air}}{C_{Glass} * C_{Air}} \quad (2)$$

$$\frac{1}{C_{SC}} = \frac{1}{C_{Glass}} + \frac{1}{C_{Stpr}} + \frac{1}{C_{Glass}} = \frac{1}{C_{Stpr}} + \frac{2}{C_{Glass}} = \frac{C_{Glass} + 2 * C_{Stpr}}{C_{Glass} * C_{Stpr}} \quad (3)$$

Each capacitance $C_{Glass}$, $C_{Drug}$, $C_{Stpr}$, and $C_{Air}$ is equal to the relative permittivity of the material ($\epsilon_{r\_Glass}$, $\epsilon^{r\_Drug}$, $\epsilon_{r\_Stpr}$, or $\epsilon_{r\_Air}$), the permittivity of vacuum (EO), the thickness of the materials ($d_{Glass}$, $d_{Drug}$, $d_{Stpr}$, or $d_{Air}$), and the area of the electrode plates surrounding the given capacitor region ($A_{FC}$, $A_{AC}$, or $A_{SC}$). For example, the capacitance of glass in the fluid chamber capacitor is equal to $\epsilon_{r\_Glass} * \epsilon_0 * A_{FC} / d_{Glass}$. The relative permittivity of each material, the permittivity of vacuum, and the thickness of each material is known. The thickness of regions that are curved or otherwise non-uniform (e.g., a circular chamber or an x-shaped plunger) may be approximated, e.g., by selecting a median thickness. A material's relative permittivity may change based on environmental conditions, such as temperature and pressure, which may be sensed and used to determine the current permittivity, as described with respect to FIG. 5. The area of the electrode plates surrounding each capacitor region changes as the stopper 230 is moved. If the electrode plates have a constant width across the syringe, e.g., if the electrode plates are rectangular, the area of the electrode plates surrounding the stopper capacitor may be constant, as the stopper has a constant size.

By substituting the definitions of capacitance as a function of relative permittivity, vacuum permittivity, thickness, and area into formulas (1)-(3) above, the following capacitances for each of the parallel capacitor regions may be obtained:

$$C_{FC} = \frac{(\epsilon_0 * A_{FC})}{\left(\frac{d_{Drug}}{\epsilon_{r\_Drug}}\right) + 2 * \left(\frac{d_{Glass}}{\epsilon_{r\_Glass}}\right)} \quad (4)$$

$$C_{AC} = \frac{(\epsilon_0 * A_{AC})}{\left(\frac{d_{Air}}{\epsilon_{r\_Air}}\right) + 2 * \left(\frac{d_{Glass}}{\epsilon_{r\_Glass}}\right)} \quad (5)$$

$$C_{SC} = \frac{(\epsilon_0 * A_{SC})}{\left(\frac{d_{Stpr}}{\epsilon_{r\_Stpr}}\right) + 2 * \left(\frac{d_{Glass}}{\epsilon_{r\_Glass}}\right)} \quad (6)$$

The capacitance across the electrodes 250*a* and 250*b*, referred to as $C_{Sensor}$, is the sum of the capacitances of the three capacitor regions:

$$C_{Sensor} = C_{FC} + C_{AC} + C_{SC} \quad (7)$$

Substituting formulas (4)-(6) into formula (7) and solving for the area $A_{FC}$ of the electrodes 250*a* and 250*b* along the fluid chamber provides the following formula for $A_{FC}$, where $A_{Sensor}$ is the total area of the electrodes 250*a* and 250*b*:

$$A_{FC} = \frac{\left(\frac{C_{Sensor}}{\epsilon_0}\right) - \frac{A_{Sensor}}{\left(\frac{d_{Air}}{\epsilon_{r\_Air}}\right) + 2 * \left(\frac{d_{Glass}}{\epsilon_{r\_Glass}}\right)} - A_{Stpr} * \left(\frac{1}{\left(\frac{d_{Stpr}}{\epsilon_{r\_Stpr}}\right) + 2 * \left(\frac{d_{Glass}}{\epsilon_{r\_Glass}}\right)} - \frac{1}{\left(\frac{d_{Air}}{\epsilon_{r\_Air}}\right) + 2 * \left(\frac{d_{Glass}}{\epsilon_{r\_Glass}}\right)}\right)}{\frac{1}{\left(\frac{d_{Drug}}{\epsilon_{r\_Drug}}\right) + 2 * \left(\frac{d_{Glass}}{\epsilon_{r\_Glass}}\right)} - \frac{1}{\left(\frac{d_{Air}}{\epsilon_{r\_Air}}\right) + 2 * \left(\frac{d_{Glass}}{\epsilon_{r\_Glass}}\right)}} \quad (8)$$

If the electrodes 250*a* and 250*b* are rectangular with a length $L_{sensor}$ and a width $W_{sensor}$, the length of the fluid chamber ($L_{FC}$) can be determined as a function of various known quantities, including the length of the stopper $L_{Stpr}$, and the capacitance measurement $C_{Sensor}$:

$$L_{FC} = \frac{\left(\frac{C_{Sensor}}{\epsilon_0 * W_{Sensor}}\right) - \frac{L_{Sensor}}{\left(\frac{d_{Air}}{\epsilon_{r\_Air}}\right) + 2 * \left(\frac{d_{Glass}}{\epsilon_{r\_Glass}}\right)} - L_{Stpr} * \left(\frac{1}{\left(\frac{d_{Stpr}}{\epsilon_{r\_Stpr}}\right) + 2 * \left(\frac{d_{Glass}}{\epsilon_{r\_Glass}}\right)} - \frac{1}{\left(\frac{d_{Air}}{\epsilon_{r\_Air}}\right) + 2 * \left(\frac{d_{Glass}}{\epsilon_{r\_Glass}}\right)}\right)}{\frac{1}{\left(\frac{d_{Drug}}{\epsilon_{r\_Drug}}\right) + 2 * \left(\frac{d_{Glass}}{\epsilon_{r\_Glass}}\right)} - \frac{1}{\left(\frac{d_{Air}}{\epsilon_{r\_Air}}\right) + 2 * \left(\frac{d_{Glass}}{\epsilon_{r\_Glass}}\right)}} \quad (9)$$

The length of the fluid chamber is related to the volume of drug in the chamber. For example, for a cylindrical syringe, the volume of the drug in the syringe $V_{drug}$ is related to the length of the fluid chamber by the following equation, where $r_{syringe}$ is the internal radius of the syringe:

$$V_{drug} = L_{FC} * \pi * r_{syringe}^2 \quad (10)$$

Furthermore, the capacitance can be expressed as a function of various known quantities and the length of the fluid chamber $L_{FC}$:

$$C_{Sensor} = (\epsilon_0 * W_{Sensor}) * \left( L_{FC} * \left(\frac{1}{\left(\frac{d_{Drug}}{\epsilon_{rDrug}}\right) + 2 * \left(\frac{d_{Glass}}{\epsilon_{rGlass}}\right)} - \frac{1}{\left(\frac{d_{Air}}{\epsilon_{rAir}}\right) + 2 * \left(\frac{d_{Glass}}{\epsilon_{rGlass}}\right)}\right) + \frac{L_{Sensor}}{\left(\frac{d_{Air}}{\epsilon_{r\_Air}}\right) + 2 * \left(\frac{d_{Glass}}{\epsilon_{r\_Glass}}\right)} + L_{Stpr} * \left(\frac{1}{\left(\frac{d_{Stpr}}{\epsilon_{r\_Stpr}}\right) + 2 * \left(\frac{d_{Glass}}{\epsilon_{r\_Glass}}\right)} - \frac{1}{\left(\frac{d_{Air}}{\epsilon_{r\_Air}}\right) + 2 * \left(\frac{d_{Glass}}{\epsilon_{r\_Glass}}\right)}\right)\right) \quad (11)$$

The relationship between the measured capacitance across the electrodes and the length of the fluid chamber can be derived in a similar manner for alternate implementations. For example, if a particular syringe system has an air gap between the electrodes and the wall of the syringe, the air gap may be incorporated as an additional series layer with an additional contribution to capacitance in the equations (1)-(3). As another example, formulas that use an exact calculation for capacitance across circular or curved surfaces may be used, rather than an approximation using the median thickness as in the example above. As another example, if a different plunger rod (e.g., a hollow plunger rod, or an x-shaped plunger rod) is used, the capacitance of the air chamber may be different. As another example, as discussed in relation to FIGS. 2 and 4, in some embodiments, the plunger rod 260 is used as an electrode, and the capacitor is formed between the plunger rod 260 and an outer electrode, e.g., electrode 250*a*. Furthermore, in an example where the capacitance sensor is used to monitor filling of a container such as a vial, the stopper may not be included. It should be understood that while other container shapes, electrode shapes, and sensor configurations may be used, for a given sensor and system geometry, the capacitance as a function of air chamber length, and fluid chamber length (or drug volume) as a function of capacitance, may be derived in a similar manner.

Example Drug Delivery System

Figure 5:
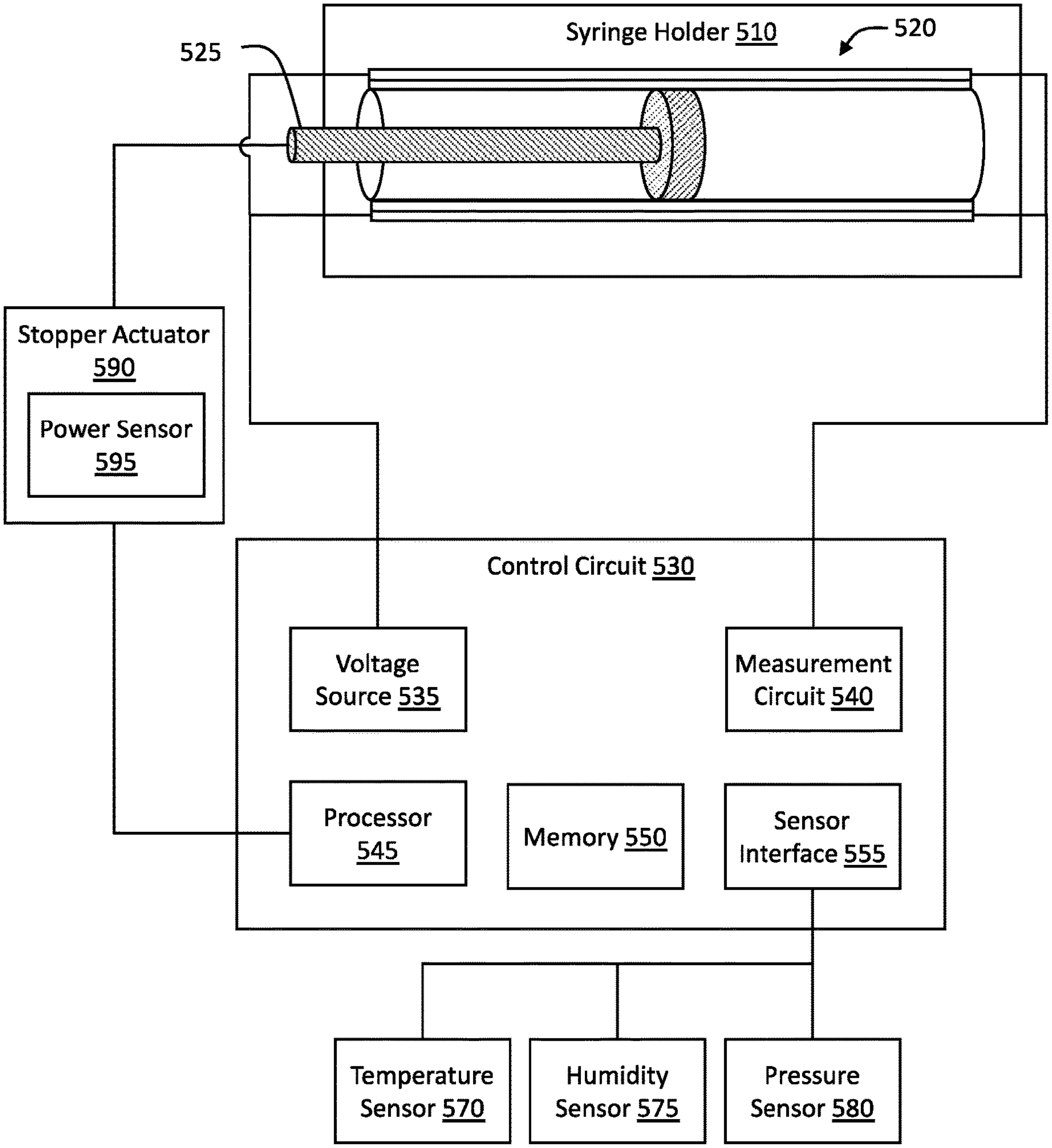
FIG. 5 is a block diagram showing a drug delivery system according to some embodiments of the present disclosure.

FIG. 5 is a block diagram showing a drug delivery system according to some embodiments of the present disclosure. The drug delivery system includes a syringe holder 510, a control circuit 530, various sensor systems 570-580, and a stopper actuator 590. The syringe holder 510 holds a syringe 520 controlled by a plunger rod 525. The control circuit 530 includes a voltage source 535, a measurement circuit 540, a processor 545, a memory 550, and a sensor interface 555 that interfaces with a temperature sensor 570, a humidity sensor 575, and a pressure sensor 580. In alternative configurations, different, fewer, and/or additional components may be included in the drug delivery system from those shown in FIG. 5. Furthermore, the functionality described in conjunction with one or more of the components shown in FIG. 5 may be distributed among the components in a different manner than described.

The syringe holder 510 is configured to hold a syringe containing a drug. The syringe holder 510, the syringe 520, and/or the plunger rod 525 provide a capacitive sensor, e.g., the capacitive sensors described with respect to FIGS. 1-4. In some embodiments, the syringe holder 510 is configured to hold one or more standard syringes, e.g., a syringe of a particular standard size and shape. In some embodiments, the syringe holder 510 includes a pair of electrodes that fit around the syringe 520 when the syringe 520 is inserted into the syringe holder 510. For example, the syringe holder 510 can be designed to accept existing FDA-approved syringes. In other embodiments, the syringe 520 (and in some embodiments, the plunger rod 525) includes the electrodes for the capacitive sensor, and the syringe holder 510 includes electrical contacts for coupling the electrodes to the control circuit 530.

The voltage source 535 connects to the electrodes to apply a voltage to the electrodes. The voltage source 535 may be the voltage source 340 or voltage source 455 shown in FIGS. 3 and 4. The applied voltage generates an electric field through at least a portion of the syringe 520, as shown in FIGS. 3 and 4. The measurement circuit 540 also connects to the electrodes of the capacitive sensor and determines a capacitance measurement $C_{Sensor}$ across the pair of electrodes, e.g., based on a measured charge. The measurement circuit 540 provides the capacitance measurement to the processor 545, and the processor 545 controls the stopper based on the capacitance measurement. In some embodiments, the processor 545 determines, based on the measured capacitance, the amount of drug remaining in the syringe. In some embodiments, the processor 545 compares the capacitance measurement to a target capacitance, and controls the stopper based on the capacitance. Various control algorithms that may be performed by the processor 545 are shown in FIGS. 6-12, described below.

The stopper actuator 590 is coupled to the plunger rod 525 to physically control the position of the plunger rod 525 and, by extension, the position of the stopper in the syringe 520. The stopper actuator 590 includes a motor or other mechanism for applying force to the plunger rod 525. The processor 545 sends instructions to the stopper actuator 590 to move the plunger rod 525. For example, the processor 545 may send an instruction to the stopper actuator 590 to apply a particular force to the plunger rod 525, or to apply force to the plunger rod 525 for a particular duration. In some embodiments, the stopper actuator 590 may be configured to pull the plunger rod 525 towards the left in the orientation shown in FIG. 5, in order to draw a drug into the syringe 520.

The processor 545 may obtain continuous or periodic capacitance readings from the measurement circuit 540 during drug delivery. For example, the processor 545 may instruct the stopper actuator 590 to apply a certain amount of power to the plunger rod 525, obtain a new capacitance measurement from the measurement circuit 540, instruct the stopper actuator 590 to apply additional power to the plunger rod 525, obtain a new capacitance measurement, etc., until the desired dose has been delivered. The stopper actuator 590 may apply a fixed amount of power with each step, or the processor 545 may instruct the stopper actuator 590 to apply an amount of power that based on the dose, an expected syringe response, desired speed of injection, and/or other factors.

In some implementations, such as emergency medicine settings, rather than using a stopper actuator 590, drug delivery may be manually controlled. In such embodiments, the capacitance sensor is used to determine the amount of a drug that was delivered to a patient. For example, the measurement circuit 540 obtains a first capacitance measurement prior to delivery, which is used as a baseline. Alternatively, a pre-filled, single-use syringe has a known volume prior to use. After manual drug delivery, the measurement circuit 540 measures the capacitance across the electrodes, and the processor 545 uses the baseline volume or capacitance and the post-delivery capacitance to calculate the volume of drug that has been delivered.

The memory 550 stores data used by the processor 545 to control delivery of the drug, calculate a volume of drug delivered, and other processes. For example, the memory 550 may store calibration data indicating, for a given drug, the amount of remaining drug that corresponds to different capacitance levels. In some embodiments, the memory 550 stores a formula, e.g., formula (9) above, for converting the measured capacitance to a length of the fluid chamber. The memory 550 may further store formula (10) to calculate a volume of drug in the fluid chamber. The memory 550 may store data characterizing the drug, such as the relative permittivity of one or more drugs that may be delivered by the syringe, and relationships between relative permittivity of a drug and environmental factors such as temperature and humidity. The memory 550 may also store other quantities used in the formulas above, such as data describing the geometry of the syringe 520 and the stopper, geometry of the electrodes, permittivity of the wall, the stopper, and air (including how permittivities vary based on humidity and temperature), etc. A process for characterizing and calibrating a drug delivery system is described in relation to FIG. 6. In some embodiments, the memory 550 stores measurements received from various sensors, such as the temperature sensor 570, humidity sensor 575, pressure sensor 580, and/or power sensor 595.

The sensor interface 555 interfaces with one or more sensors included in the drug delivery system or in communication with the drug delivery system. The sensors include a temperature sensor 570, a humidity sensor 575, and a pressure sensor 580. As noted above, the relative permittivity of air and the relative permittivity of the drug may vary based on environmental conditions, such as temperature and humidity.

In some embodiments, the temperature sensor 570 measures ambient temperature. In some embodiments, the temperature sensor 570 is included in the syringe holder 510 and measures the temperature of the fluid chamber. In some embodiments, the temperature sensor 570 is included in the syringe holder 510 and measures the temperature of the air chamber. In some embodiments, the drug delivery system includes multiple temperature sensors, e.g., one to measure temperature of the drug, and another to measure temperature of the air. In some embodiments, the control circuit 530 may receive another temperature input, e.g., the drug delivery device may include a user interface with which an operator can input a temperature of a drug (e.g., if the drug is stored in a refrigerator or held at an ambient temperature prior to delivery to a patient). In some embodiments, the memory 550 may store a typical temperature for a drug, e.g., 33 degrees Fahrenheit for a drug that is stored in a refrigerator, and 72 degrees Fahrenheit for a drug that is stored at ambient temperature.

The relative permittivity of one or more sensor dielectrics (e.g., the relative permittivity of air) varies based on humidity in the air. In some embodiments, the humidity sensor 575 measures ambient humidity. In some embodiments, the humidity sensor 575 is included in the syringe holder 510 and measures the humidity of the air chamber. In some embodiments, the control circuit 530 may receive another humidity input, e.g., the drug delivery device may include a user interface with which an operator can input a humidity reading.

The pressure sensor 580 measures a pressure within the fluid chamber of the syringe 520. The pressure sensor 580 may be included in the syringe holder 510 or within the syringe 520 itself to measure the pressure within the fluid chamber. The pressure measurement may be used to detect an occlusion or a leakage in the syringe, as described with respect to FIG. 10.

As noted above, the stopper actuator 590 is coupled to the plunger rod 525 to physically control the position of the plunger rod 525 and, by extension, the position of the stopper in the syringe 520. The stopper actuator 590 may include a power sensor 595 that measures electrical power supplied to a motor of the stopper actuator 590. The power supplied to the stopper actuator 590 is referred to as the stopper actuator power. The power measurement may be used to detect an occlusion or a leakage in the syringe, as described with respect to FIG. 10.

In some embodiments, the processor 545 may output the amount of remaining drug in the syringe 520. For example, the drug delivery system may have a display screen (not shown in FIG. 5) for displaying the amount of remaining drug and/or the amount of drug that has been delivered. The drug delivery system may be in wireless or wired communication with one or more other devices, and transmit the amount of remaining or delivered drug to the other device(s). As described with respect to FIGS. 10-12, the processor 545 may perform various error and failure detection processes. A display or other user interface components (e.g., alert or warning lights or sounds) of the drug delivery system or a connected device may provide output displays or signals indicating whether an error or failure was detected, and in some embodiments, indicating a cause of the error or failure.

Process for Characterizing and Calibrating a Capacitive Sensor

As noted above, the relative permittivities of air and of drugs are generally not uniform across different environmental conditions. For example, the permittivity of dielectric materials in the capacitive sensor may vary based on temperature and/or humidity. In certain applications, a drug delivery system using a capacitive sensor may be subjected to a wide range of environmental conditions, e.g., the capacitive sensor may be incorporated into an epinephrine autoinjector that can be used in indoor and outdoor environments, or in an insulin monitoring and injection device configured to be worn by a patient and inject insulin throughout the day. In such implementations, the drug delivery device may include the temperature and humidity sensors 570 and 575 described above, or communication circuitry configured to receive such measurements from external sensors. Furthermore, the drug delivery system is calibrated to accurately characterize the capacitance response based on temperature and humidity.

Figure 6:
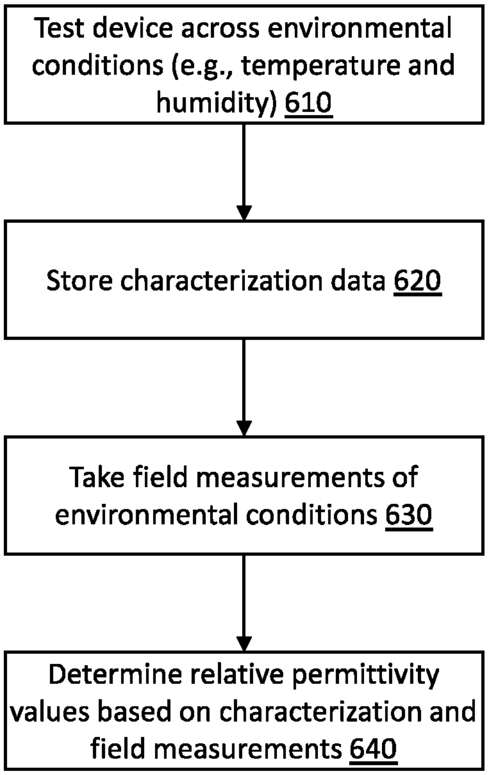
FIG. 6 is a flow diagram showing a process for characterizing and calibrating a capacitive sensor of a drug delivery system, according to some embodiments of the present disclosure.

FIG. 6 is a flow diagram showing a process for characterizing and calibrating a capacitive sensor of a drug delivery system, according to some embodiments of the present disclosure. To characterize the drug delivery system, and operator tests 610 the device across various environmental conditions, e.g., various temperature and humidity conditions. For example, a drug delivery device is operated in an environment in which temperature and humidity may be controlled, and the device is operated under a range of temperatures and/or humidity conditions. During calibration, the volume of drug in the fluid chamber is known, and the characterization data captures capacitance measurements for a known volume of a known drug under varying environmental conditions, which may be measured by the temperature and/or humidity sensors 570 and 575.

The memory 550 stores 620 the characterization data. In some embodiments, the calibration data is stored in the memory 550 as one or more formulas used to calculate permittivity of a given material based on temperature and/or humidity measurements. Alternatively, the calibration data may be stored in the memory 550 as a lookup table. In some embodiments, the calibration data includes the permittivity response of air to variation in temperature and/or humidity. In some embodiments, the calibration data includes the permittivity response of a particular drug to variation in temperature and/or humidity. In some embodiments, the permittivity response of a drug to changes in humidity are minimal and may be ignored. In some embodiments, the permittivity response of water or saline to changes in temperature is stored and used as an estimate of the permittivity of the drug.

To calibrate the drug delivery device during operation (e.g., prior to delivering drug to a patient), the drug delivery device (e.g., the humidity sensor 575 and temperature sensor 570) take 630 field measurements of the environmental conditions. The processor 545 receives the measurements and determines 640 the relative permittivity values for the drug and for the air based on the characterization data in memory 550 and the field measurements. These permittivity values are used in the control processes described in relation to FIGS. 7-12.

In some implementations (e.g., a hospital setting), the environment is highly controlled with limited variation in temperature and, in some cases, little variation in humidity. In such implementations, one or both of the temperature and/or humidity characterization and calibration may be omitted.

Process for Controlling Drug Delivery Based on Capacitance

Figure 7:
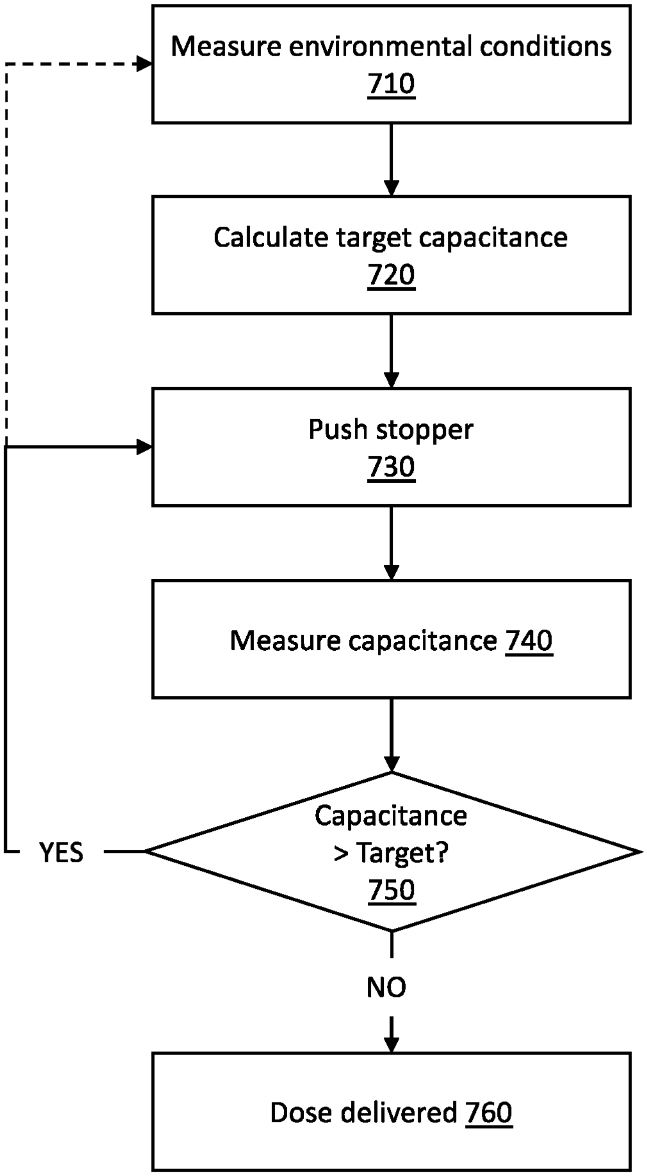
FIG. 7 is a flow diagram showing a process for controlling drug delivery using capacitance measurements, according to some embodiments of the present disclosure.

FIG. 7 is a flow diagram showing a process for controlling drug delivery using capacitance measurements, according to some embodiments of the present disclosure. A drug delivery system measures 710 environmental conditions, such as temperature and humidity. For example, the sensor interface 555 receives a temperature measurement from the temperature sensor 570 and a humidity measurement from the humidity sensor 575, and the sensor interface 555 passes the measurements to the processor 545. As noted above, relative permittivity of sensor dielectrics may vary based on temperature and humidity. For example, the relative permittivity of air in the air chamber, and thus the capacitance across the air chamber, may depend on the humidity. In addition, the relative permittivity of the air in the air chamber and the drug in the fluid chamber, and thus the capacitance across each of these chambers, may depend on the temperature.

The drug delivery system (e.g., the processor 545) calculates 720 a target capacitance for a dose of the drug to be delivered based on the environmental conditions. For example, the processor 545 determines the change in capacitance expected for a particular volume of drug based on the relative permittivities associated with the measured environmental conditions. In some embodiments, the processor 545 receives a baseline capacitance measurement from the measurement circuit 540, i.e., the capacitance across the syringe before a drug dose is delivered. The processor 545 may calculate the target capacitance based on the baseline capacitance. In particular, the target capacitance is equal to the baseline capacitance minus the change in capacitance expected for delivery of the dosage volume. The dosage volume can be expressed as $\Delta V_{dose}=\Delta L_{FC}*\pi*(r_{syringe})^2$, where $\Delta L_{FC}$ is the change in the length of the fluid chamber, which is related to the capacitance according to formulas (9) and (11).

Having calculated the target capacitance, the drug delivery system pushes 730 the stopper to expel at least a portion of the drug from the fluid chamber. For example, the processor 545 instructs the stopper actuator 590 to push the plunger rod 525, which pushes the stopper. As noted with respect to FIG. 5, the stopper actuator 590 may apply a fixed amount of power with each step, or the processor 545 may instruct the stopper actuator 590 to apply an amount of power that based on the dose, an expected syringe response, desired speed of injection, and/or other factors. After pushing the stopper, the drug delivery system measures 740 the capacitance across the pair of electrodes of the capacitive sensor. For example, the processor 545 instructs the voltage source 535 to apply a voltage across the electrodes 250, which generate an electric field through the syringe, and the measurement circuit 540 measures the capacitance across the electrodes 250 and passes the capacitance measurement to the processor 545.

The drug delivery system compares 750 the measured capacitance to the target capacitance. If the measured capacitance is greater than the target capacitance, this indicates that a portion of the dose of the drug remains in the syringe, and the drug delivery system returns to step 730 and again pushes the stopper. In some embodiments, the drug delivery system instead returns to step 710, as indicated by the dotted line, and repeats the temperature and humidity measurements and re-calculates the target capacitance before an additional portion of the drug dose is delivered. In some embodiments, the drug delivery system returns to step 710 periodically, e.g., every 10 seconds or every 5 minutes, and returns to step 730 the rest of the time. If, at decision 750, the measured capacitance is not greater than the target capacitance, the dose has been delivered 760, and the drug delivery system ends the drug delivery process.

In some embodiments, step 730 is performed in parallel with steps 740 and 750. In such embodiments, the stopper actuator 590 continually pushes the plunger. The measurement circuit 540 obtains periodic capacitance measurements as the plunger is being pushed. The processor 545 compares the periodic measurements to the target capacitance, and the processor 545 instructs the stopper actuator 590 to stop pushing the stopper after the target capacitance is reached.

Process for Controlling Delivery of a Volume of Drug

Figure 8:
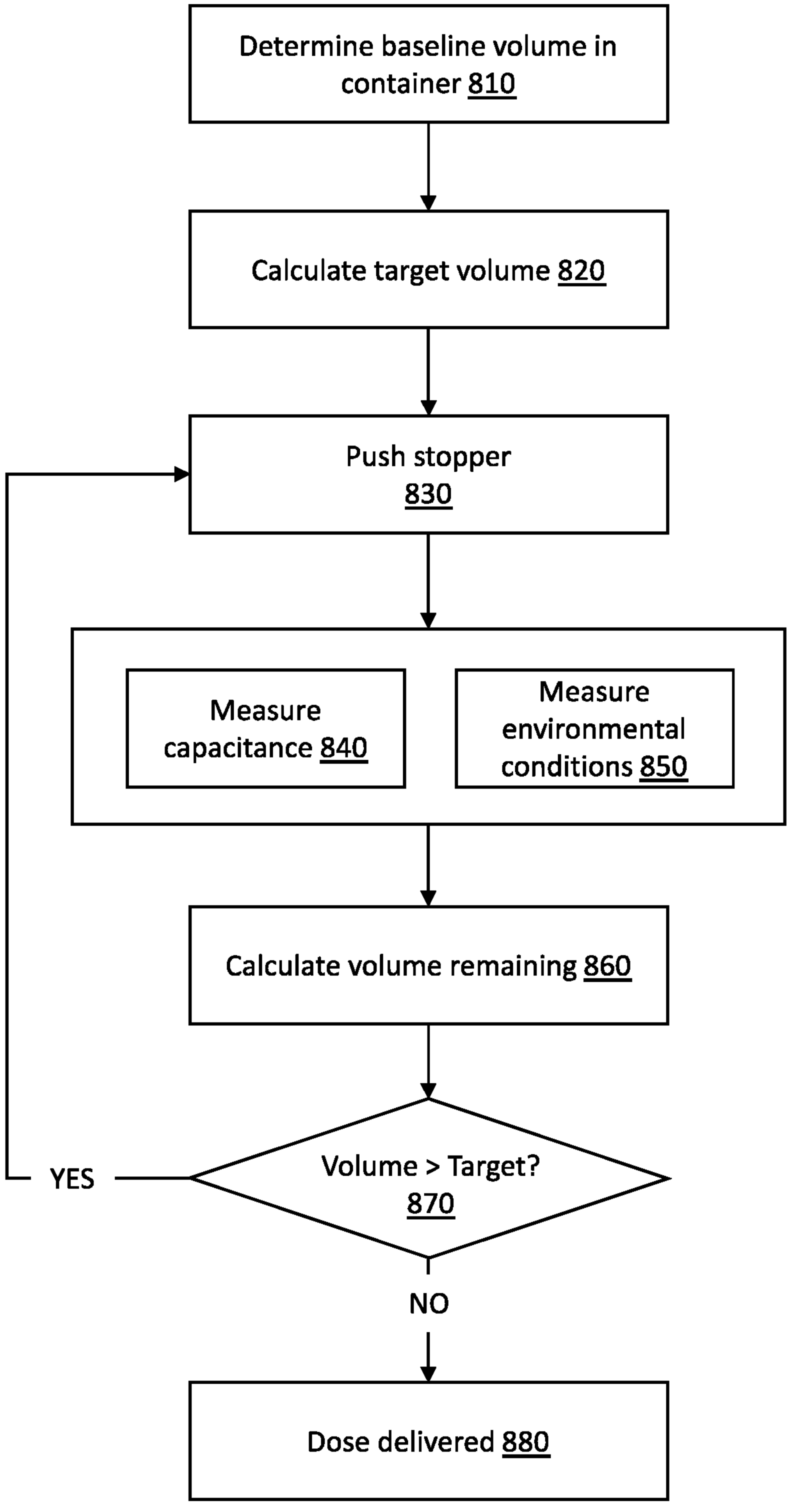
FIG. 8 is a flow diagram showing a process for controlling delivery of a volume of drug based on capacitance measurements, according to some embodiments of the present disclosure.

FIG. 8 is a flow diagram showing a process for controlling delivery of a volume of drug based on capacitance measurements, according to some embodiments of the present disclosure. The drug delivery system determines 810 a baseline pre-delivery volume of drug in the container, e.g., a syringe. For example, the processor 545 receives a baseline capacitance measurement from the measurement circuit 540, i.e., the capacitance across the syringe before a drug dose is delivered, and the processor 545 calculates the baseline volume of drug in the fluid chamber based on the capacitance measurement. The processor may calculate the baseline volume of drug from the capacitance measurement according to formulas (9) and (10). The processor 545 may receive environmental measurements, such as humidity and temperature, determine the permittivities of the air and drug based on the environmental measurements, and use the permittivities of air and the drug to calculate the baseline volume.

The drug delivery system calculates 820 a target volume for the syringe based on the baseline volume. For example, the processor 545 subtracts a dosage volume from the baseline volume to obtain the target volume. The target volume is the volume of drug remaining in the syringe after the dose has been delivered.

The drug delivery system pushes 830 the stopper to expel at least a portion of the drug from the fluid chamber. For example, the processor 545 instructs the stopper actuator 590 to push the plunger rod 525, which pushes the stopper. As noted with respect to FIG. 5, the stopper actuator 590 may apply a fixed amount of power with each step, or the processor 545 may instruct the stopper actuator 590 to apply an amount of power that based on the dose, an expected syringe response, desired speed of injection, and/or other factors.

After pushing the stopper, the drug delivery system measures 840 the capacitance across the pair of electrodes of the capacitive sensor. For example, the processor 545 instructs the voltage source 535 to apply a voltage across the electrodes 250, which generate an electric field through the syringe, and the measurement circuit 540 measures the capacitance across the electrodes 250 and passes the capacitance measurement to the processor 545. The drug delivery system also measures 850 environmental conditions, such as temperature and humidity. For example, the sensor interface 555 receives a temperature measurement from the temperature sensor 570 and a humidity measurement from the humidity sensor 575, and the sensor interface 555 passes the measurements to the processor 545. Alternatively, if the environmental conditions were previously measured and can be assumed to be stable throughout the drug delivery process, the processor 545 may instead access previous measurements of the environmental conditions (e.g., measurements stored in the memory 550).

The drug delivery system calculates 860 the volume of drug remaining in the syringe based on the measured capacitance and the measured environmental conditions. The processor 545 may calculate the volume of drug remaining from the capacitance measurement and the permittivities (determined based on the measured environmental conditions) according to formulas (9) and (10).

The drug delivery system (e.g., the processor 545) compares the volume of drug remaining to the target volume. If the measured volume remaining is greater than the target volume, the drug delivery system returns to step 830 and again pushes the stopper. If the volume is equal to, or less than, the target volume, the dose has been delivered 880, and the drug delivery system ends the drug delivery process.

In some embodiments, step 830 is performed in parallel with steps 840 and 850. In such embodiments, the stopper actuator 590 continually pushes the plunger. The measurement circuit 540 obtains periodic capacitance measurements as the plunger is being pushed, and the processor 545 calculates the remaining volume. The processor 545 compares the periodic volume measurements to the target volume, and the processor 545 instructs the stopper actuator 590 to stop pushing the stopper after the target volume is reached.

While the process shown in FIG. 8 uses volume to determine whether the dose has been delivered, in some embodiments the processor 545 converts dosage volumes to fluid chamber lengths, and the processor 545 compares the measured fluid chamber length to a target fluid chamber length.

Process for Filling a Container Based on Capacitance Measurements

Figure 9:
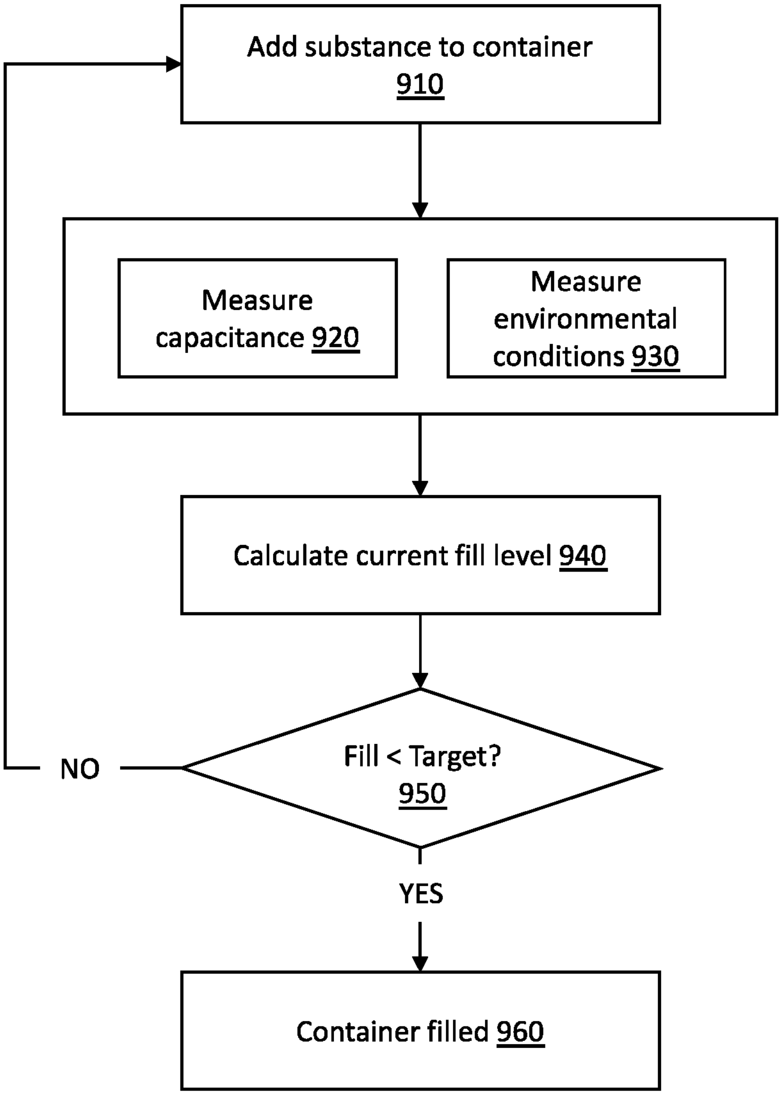
FIG. 9 is flow diagram showing a process for filling a container with a drug based on capacitance measurements, according to some embodiments of the present disclosure.

FIG. 9 is flow diagram showing a process for filling a container with a drug based on capacitance measurements, according to some embodiments of the present disclosure. For example, the drug delivery system shown in FIG. 5 may use this process to fill the syringe 520. In this example, the stopper actuator 590 may pull the stopper to fill the fluid chamber with a drug. In other examples, other types of syringe control systems or, more generally, container control systems may use this process.

The container control system adds 910 a substance, e.g., a drug, to a container. In the syringe example, the container control system pulls a stopper to draw fluid into the fluid chamber. In other cases, a container control system may cause a fluid to move into a container in another manner, e.g., by pouring a fluid into a vial. The container control system may fill a fixed or variable amount of the substance into the container in each step.

After adding some of the substance to the container, the container control system measures 920 the capacitance across the pair of electrodes of the capacitive sensor. For example, if the drug delivery system shown in FIG. 5 is filling the syringe 200, the processor 545 instructs the voltage source 535 to apply a voltage across the electrodes 250, which generate an electric field through the syringe, and the measurement circuit 540 measures the capacitance across the electrodes 250 and passes the capacitance measurement to the processor 545. The container control system also measures 930 environmental conditions, such as temperature and humidity. For example, the sensor interface 555 receives a temperature measurement from the temperature sensor 570 and a humidity measurement from the humidity sensor 575, and the sensor interface 555 passes the measurements to the processor 545. Alternatively, if the environmental conditions were previously measured and can be assumed to be stable throughout the container filling process, the processor 545 may instead access previous measurements of the environmental conditions (e.g., measurements stored in the memory 550).

The container control system calculates 940 the current fill level (e.g., the volume of drug in the container) based on the measured capacitance and the measured environmental conditions. For example, the container control system may calculate the length of the fluid chamber from the capacitance measurement and the permittivities (determined based on the measured environmental conditions) according to equation (9). In some embodiments, the container control system further calculates the volume of drug in the container according to equation (10).

The container control system compares 950 the fill level to a target fill level. If the measured fill level is less than the target fill level, the container control system returns to step 910 and adds additional substance to the container. If the fill level is equal to, or greater than, the target fill level, the container is filled 960, and the container control system ends the filling process. In other embodiments, the container control system determines a target capacitance associated with a target fill level, and compares measured capacitances to the target capacitance, similar to the process shown in FIG. 7.

Detecting Device Errors During Drug Delivery

During injection of the drug, the capacitance sensor periodically or continually measures capacitance across the syringe. During drug delivery, the drug delivery system expects to observe a change in capacitance, a change in the length of the fluid chamber, or a change in the volume of the drug remaining in the syringe as the stopper is expelling drug from the syringe. If the capacitance and/or associated length or volume does not change by an expected amount during the injection, this indicates a failure that may be caused by a blockage. Additional sensors, such the pressure sensor 580 for measuring pressure in the fluid chamber, and the power sensor 595 for measuring the stopper actuator power supplied to a motor for moving the plunger rod 525, provide additional data that can be used to identify a failure mode. For example, the power and/or pressure measurements may be used to determine if the syringe has an occlusion or a leak. Further, if the pressure and/or power measurements indicate that a failure is due to an occlusion or leak, this can assist an operator in ruling out other potential factors, such as a fault in the stopper actuator 590.

Figure 10:
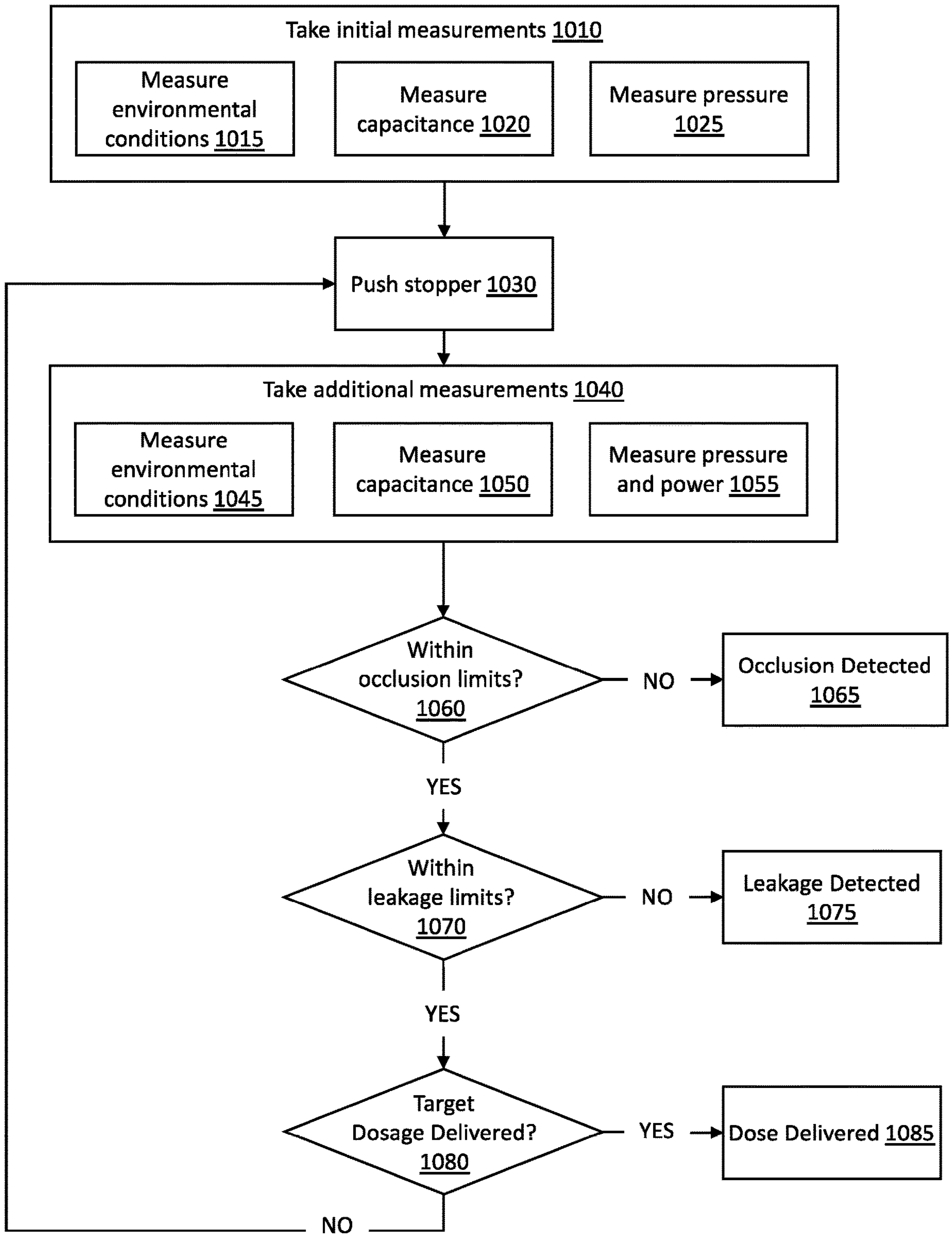
FIG. 10 is a flow diagram showing a process for detecting device errors during drug delivery based on capacitance measurements, according to some embodiments of the present disclosure.

FIG. 10 is a flow diagram showing a process for detecting device errors during drug delivery based on capacitance measurements, according to some embodiments of the present disclosure. The process shown in FIG. 10 may be integrated into a drug delivery procedure, such as either of the processes shown in FIG. 7 or 8.

Prior to delivery, the drug delivery system takes 1010 various initial measurements from various sensors and measurement circuits. The drug delivery system measures 1015 environmental conditions, such as temperature and humidity. The drug delivery system also measures 1020 capacitance across the syringe. Step 1015 is similar to steps 710 and 850, described with respect to FIGS. 7 and 8, respectively. Step 1020 is similar to steps 740 and 840, described with respect to FIGS. 7 and 8, respectively. In some embodiments, the drug delivery system also measures 1025 an initial pressure in the fluid chamber. In particular, the pressure sensor 580 measures the pressure in the fluid chamber of the syringe 520. The sensor interface 555 receives the pressure measurement and passes the pressure measurement to the processor 545. Steps 1015, 1020, and 1025 may be performed in parallel, as shown in FIG. 10, or in series, in any order.

After taking the initial measurements, the drug delivery system pushes 1030 the stopper to deliver a portion of the drug from the syringe. Step 1030 is similar to steps 730 and 830 described with respect to FIGS. 7 and 8, respectively. During or shortly after pushing the stopper, the drug delivery system takes 1040 additional measurements from the sensors and measurement circuits. In some embodiments, the drug delivery system measures 1045 the environmental conditions, such as humidity and temperature, again. In other embodiments, step 1045 is not performed, e.g., the drug delivery system assumes the environmental conditions measured at step 1010 are stable throughout the delivery process. The drug delivery system (e.g., the measurement circuit 540) measures 1050 capacitance across the syringe during or after the stopper is pushed at step 1030. The drug delivery system measures 1055 the stopper actuator power and a pressure in the fluid chamber. For example, while the stopper actuator 590 pushes the stopper in step 1030, the power sensor 595 measures the electrical power delivered to the stopper actuator 590, which pushes the plunger rod 525. The power measurement may be received by the processor 545, as shown in FIG. 5, or passed to the sensor interface 555, which transmits the power measurement to the processor 545. The pressure sensor 580 measures the pressure in the fluid chamber of the syringe 520 during and/or after step 1030. The sensor interface 555 receives the pressure measurement and passes the pressure measurement to the processor 545. Steps 1045, 1050, and 1055 may be performed in parallel or in series, and one or more of steps 1045, 1050, and 1055 may be performed while the stopper is being pushed in step 1030.

The drug delivery system compares 1060 at least some of the measurements to occlusion limits to determine if the syringe is occluded, e.g., there is a blockage in the syringe limiting flow of the drug out of the syringe. For example, the processor 545 compares the initial capacitance measurement from step 1020 to the capacitance measurement from step 1050, after the stopper has been pushed. If the difference between the two capacitances is less than expected for the power supplied to the motor, this indicates that the syringe has experienced a failure, such as an occlusion blocking the drug outlet, or a failure of the stopper actuator 590.

In one embodiment, the processor 545 compares the difference between two capacitance measurements to an error threshold, and if the difference is less than an error threshold, determines that the drug delivery system has experienced a failure. For example, if the stopper actuator is expected to delivery 1 mL of a drug at step 1030, the error threshold may be the capacitance difference expected for 0.8 mL. In some examples, the processor 545 compares the capacitance difference to an expected range, e.g., a capacitance difference expected for 0.9 mL to 1.1 mL of drug delivered. If the measured capacitance difference is outside the expected range, this indicates an error in the delivery system.

The drug delivery system may use additional measurements to determine a type of failure, e.g., an occlusion or a stopper actuator failure. For example, if the pressure measurement exceeds a threshold pressure measurement, this indicates that the failure is an occlusion. If the power measurement exceeds a threshold power measurement, this indicates that the failure is an occlusion. A high power and high pressure in the fluid chamber indicate that the stopper actuator 590 pushed the stopper, but the drug did not exit the syringe outlet. By contrast, if the pressure and/or power measurement are below a threshold pressure or power, this suggests that the stopper was not pushed, which may indicate a failure at the electrical supply to the stopper actuator 590, a failure at the stopper actuator 590, or another issue with the drug delivery system outside of the syringe 520. In some embodiments, either pressure or power are used to detect an occlusion; in other embodiments, both pressure and power are used. If the measurements are not within the occlusion limits, an occlusion is detected 1065. The drug delivery system may output an alert or error to the user, e.g., using a display or other form of notification on the drug delivery device, or by transmitting an alert to another system.

If the measurements are within the occlusion limits, the drug delivery system compares 1070 at least some of the measurements to leakage limits to determine if the syringe is leaking. If the pressure measurement is below a threshold pressure measurement, this indicates that the failure is a leakage. If the power measurement is less than a threshold power measurement, this indicates that the failure is a leakage. In some embodiments, either pressure or power are used to detect a leakage; in other embodiments, both pressure and power are used. The threshold pressure for a leakage may be a different threshold from the threshold pressure for an occlusion. The syringe may have an expected pressure range, and a measured pressure below the lower end of the expected pressure range indicates a leakage, and a measured pressure above the upper end of the expected pressure range indicates an occlusion. If the measurements are not within the leakage limits, a leakage is detected 1075. The drug delivery system may output an alert or error to the user, e.g., using a display or other form of notification on the drug delivery device, or by transmitting an alert to another system. In some embodiments, step 1070 is performed in parallel with step 1060, or the order of steps 1070 and 1060 are reversed.

If the measurements are within the leakage limits, the drug delivery system determines 1080 if the target dosage has been delivered. For example, the drug delivery system compares the capacitance measurement to a target capacitance, as described with respect to FIG. 7, or the drug delivery system compares a volume measurement derived from the capacitance measurement to a target volume, as described with respect to FIG. 8. If the target dosage has been delivered 1085, the drug delivery process ends. If the target dosage has not been delivered, the process returns to step 1030.

Confirming Drug Identity and Condition

The capacitive sensor described above can also be used to determine if an expected drug is in the container, and to determine whether the drug has fouled. If a drug has been improperly stored (e.g., not refrigerated), is past an expiration date, has been contaminated, or has changed composition for another reason, the permittivity of the drug may change. In addition, different drugs may have different relative permittivities. If the expected volume of the drug is known (e.g., the drug is in a pre-filled syringe, or a vial is filled to a known capacity), the capacitance across the container may be measured and compared to an expected capacitance measurement calculated based on the known volume and the known relative permittivity of the expected drug. If the measured capacitance is different from the expected capacitance, or differs by more than a given tolerance, this indicates that the drug may have fouled and/or that the expected drug is not in the container.

Figure 11:
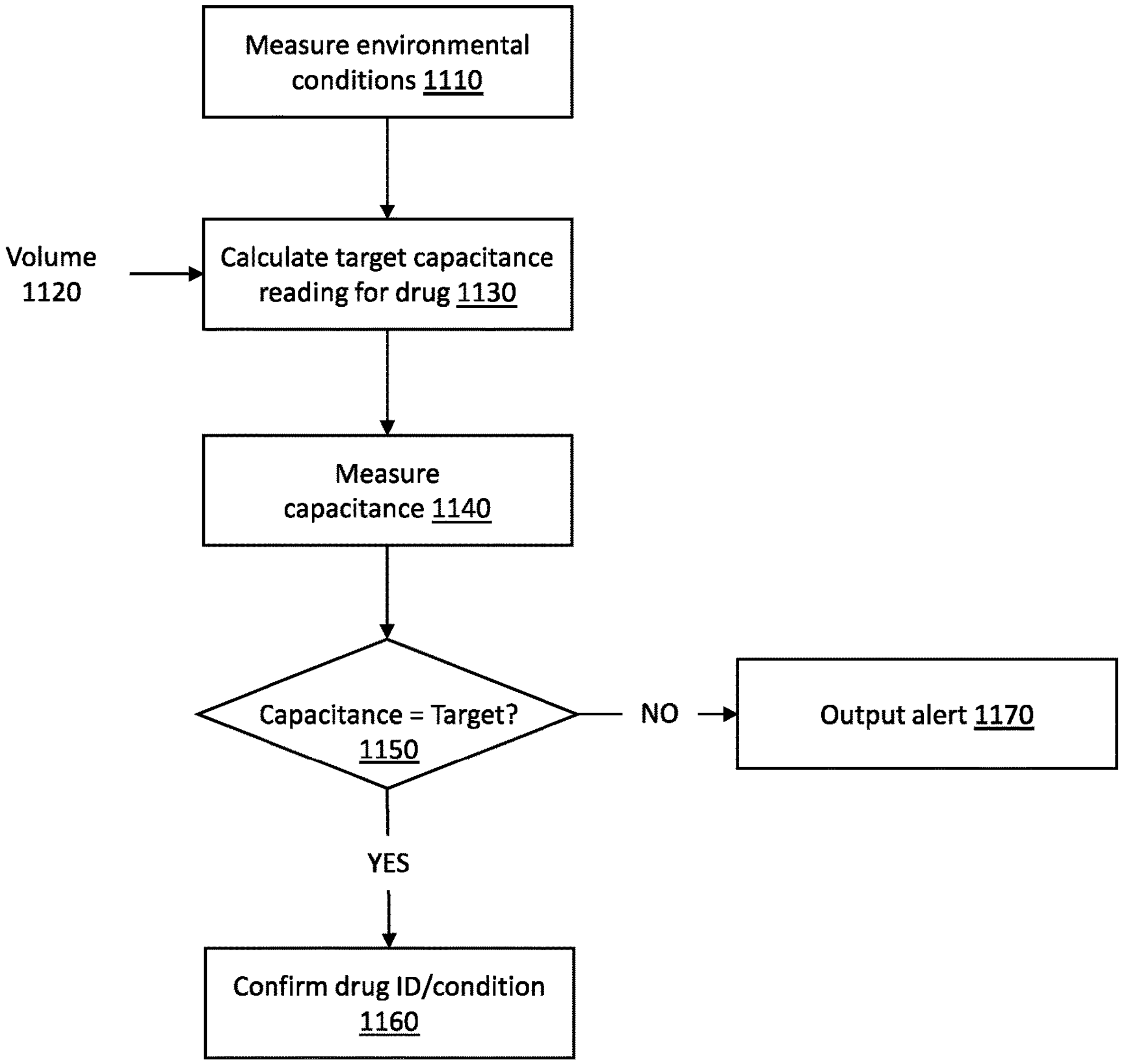
FIG. 11 is a flow diagram showing a process for confirming the identity and condition of a drug, according to some embodiments of the present disclosure.

FIG. 11 is a flow diagram showing a process for confirming the identity and condition of a drug, according to some embodiments of the present disclosure. The process shown in FIG. 11 may be performed prior to a drug delivery process, e.g., prior to either of the processes shown in FIGS. 7 and 8. The drug delivery system measures 1110 the environmental conditions, such as temperature and humidity. Step 1110 is similar to steps 710 and 850, described with respect to FIGS. 7 and 8, respectively. The drug delivery system receives the expected volume 1120 of the drug (e.g., from the memory 550), and based on the volume 1120 and environmental conditions, the drug delivery system (e.g., the processor 545) calculates 1130 a target capacitance reading for the drug. The target capacitance is an expected capacitance across the syringe based on the volume of the drug and the relative permittivities of the drug and of air under the current environmental conditions. In other embodiments, the memory 550 stores a target capacitance, e.g., a lookup table of target capacitances for different environmental conditions, and the processor 545 retrieves the target capacitance for the drug from memory 550.

The drug delivery system measures 1140 capacitance across the syringe. Step 1140 is similar to steps 740 and 840, described with respect to FIGS. 7 and 8, respectively. The drug delivery system (e.g., the processor 545) compares 1150 the measured capacitance to the target capacitance. If the measured capacitance is not equal to the target capacitance, or is within an acceptable error range from the target capacitance, the drug delivery system outputs an alert indicating that the drug in the syringe is not the expected drug, e.g., the drug has fouled, or the wrong drug is in the container. The drug delivery system may output an alert or error to the user, e.g., using a display or other form of notification on the drug delivery device, or by transmitting an alert to another system. If the measured capacitance is equal to the target capacitance, or the measured capacitance is within an acceptable error range from the target capacitance, the drug delivery system confirms 1160 the identity and condition of the drug, e.g., that the drug has not fouled, and that the expected drug is in the syringe.

Leakage Detection

The capacitive sensor described above can also be used to detect leakage within the drug delivery system by monitoring capacitance, or a quantity (e.g., length of the fluid chamber or volume of drug) derived from the capacitance measurement. Leakage may be detected before drug delivery, e.g., by detecting a change in capacitance or volume during a time period during which the volume of drug in the syringe is expected to remain constant. As described with respect to FIG. 10, additional data from pressure and power sensors increase confidence to the assessment, and may be used to determine a specific failure mode. The leakage detection algorithm may be used for other containers, e.g., to detect leakages in vials or vessels used for storing liquids.

Figure 12:
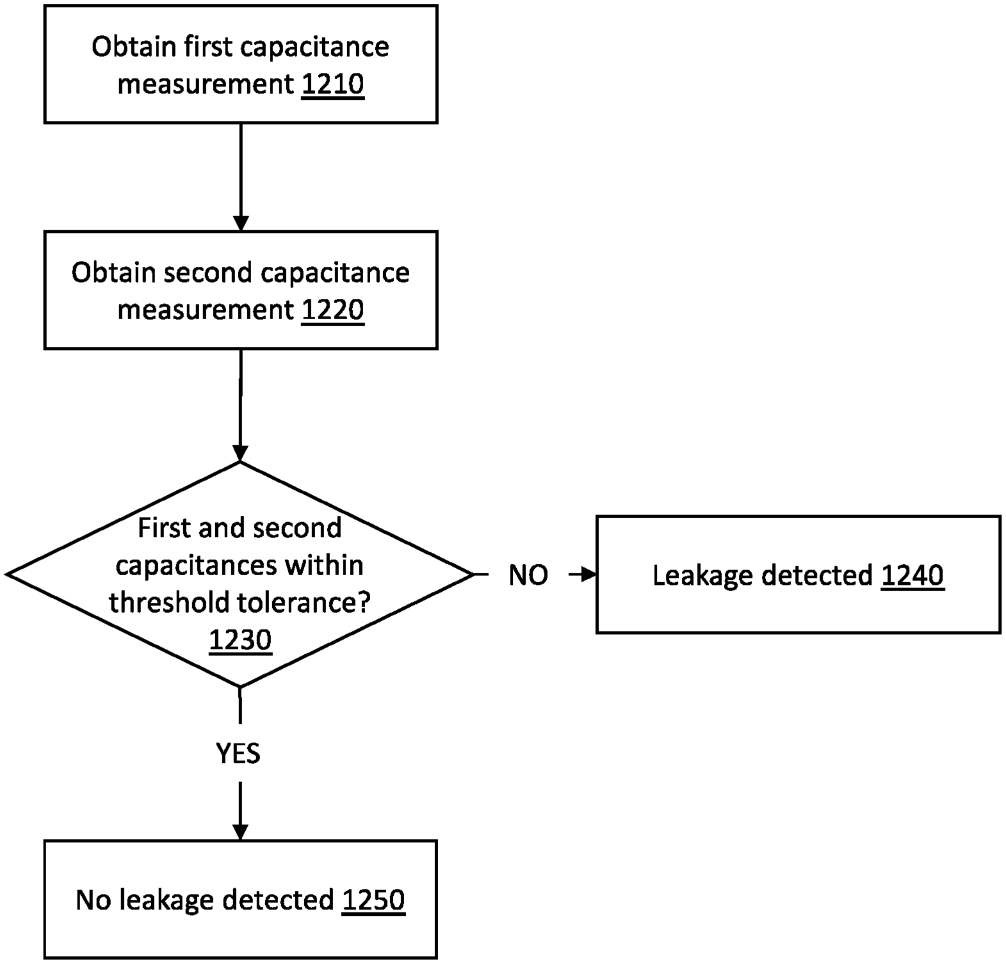
FIG. 12 is a flow diagram showing a process for detecting leakage in a container based on capacitance, according to some embodiments of the present disclosure.

FIG. 12 is a flow diagram showing a process for detecting leakage in a container based on capacitance, according to some embodiments of the present disclosure. A capacitive sensor, such as any of the capacitive sensors shown in FIGS. 1-5, obtains 1210 a first capacitance measurement. The capacitive sensor obtains 1220 a second capacitance measurement after a period of time has passed, e.g., one minute. A circuit (e.g., processor 545) compares 1130 the first and second capacitance to determine whether they are within a specific error tolerance of each other. If the capacitances are not within the error tolerance, the circuit detects 1240 a leakage. For example, the processor 545 generates an alert, and a user interface of the drug delivery system may output an alert or error to the user, e.g., using a display or other form of notification on the drug delivery device, or by transmitting an alert to another system. If the capacitances are within the error tolerance, no leakage is detected.

Other Implementation Notes, Variations, and Applications

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

In one example embodiment, any number of electrical circuits of the figures may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular arrangements of components. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more components. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of this Specification.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. Note that all optional features of the systems and methods described above may also be implemented with respect to the methods or systems described herein and specifics in the examples may be used anywhere in one or more embodiments.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph (f) of 35 U.S.C. Section 112 as it exists on the date of the filing hereof unless the words "means for" or "step for" are specifically used in the particular claims; and (b) does not intend, by any statement in the Specification, to limit this disclosure in any way that is not otherwise reflected in the appended claims.

What is claimed is:

1. A method for monitoring delivery of a drug, the method comprising:

measuring a capacitance across a pair of electrodes, the pair of electrodes arranged along either side of a container, the container comprising an air chamber, a fluid chamber, and a stopper separating the air chamber from the fluid chamber, wherein the measured capacitance is a first capacitance;

determining, based on the measured capacitance, a volume of a drug in the fluid chamber;

comparing the volume of the drug in the fluid chamber to a target volume;

in response to the volume of the drug in the fluid chamber being greater than the target volume, instructing a stopper actuator to expel at least a portion of the drug from the fluid chamber;

after instructing the stopper actuator to expel the drug from the fluid chamber, measuring a second capacitance across the pair of electrodes; and in response to a difference between the first capacitance and the second capacitance being less than an error threshold, determining that a failure has occurred.

2. The method of claim 1, further comprising:

receiving a temperature measurement from a temperature sensor; and determining the volume of the drug in the fluid chamber based on the temperature measurement, wherein a relative permittivity of sensor dielectric depends on temperature.

3. The method of claim 1, further comprising:

receiving a humidity measurement from a humidity sensor; and determining the volume of the drug in the fluid chamber based on the humidity measurement, wherein a relative permittivity of sensor dielectric depends on humidity.

4. The method of claim 1, further comprising:

measuring a baseline volume of the drug in the fluid chamber prior to expelling the drug from the fluid chamber; and calculating the target volume based on the baseline volume.

5. The method of claim 1, further comprising:

receiving at least one of a fluid chamber pressure from a pressure sensor and a stopper actuator power from a power sensor; and in response to at least one of the fluid chamber pressure exceeding a threshold pressure and the stopper actuator power exceeding a threshold power, determining that the failure is an occlusion.

6. The method of claim 1, further comprising:

receiving at least one of a fluid chamber pressure from a pressure sensor and a stopper actuator power from a power sensor; and in response to at least one of the fluid chamber pressure being lower than a threshold pressure and the stopper actuator power being lower than a threshold power, determining that the failure is a leakage.

7. The method of claim 1, further comprising:

prior to instructing the stopper actuator to expel the drug from the fluid chamber, performing a leakage detection procedure comprising:

obtaining a first capacitance measurement;

obtaining a second capacitance measurement a period of time after the first capacitance measurement; and comparing the first capacitance measurement to the second capacitance measurement to determine whether the second capacitance measurement is within a threshold tolerance of the first capacitance measurement.

8. A method for delivering a drug comprising:

determining a target capacitance for a drug dose;

measuring a capacitance across a pair of electrodes, the pair of electrodes arranged along either side of a container, the container comprising an air chamber, a fluid chamber, and a stopper separating the air chamber from the fluid chamber, the measured capacitance is a first capacitance;

comparing the measured capacitance to the target capacitance;

in response to the measured capacitance being greater than the target capacitance, instructing a stopper actuator to expel at least a portion of the drug from the fluid chamber;

after instructing the stopper actuator to expel the drug from the fluid chamber, measuring a second capacitance across the pair of electrodes; and in response to a difference between the first capacitance and the second capacitance being less than an error threshold, determining that a failure has occurred.

9. The method of claim 8, further comprising:

receiving a temperature measurement from a temperature sensor; and determining the target capacitance for the drug dose based on the temperature measurement, wherein a relative permittivity of sensor dielectric depends on temperature.

10. The method of claim 8, further comprising:

receiving a humidity measurement from a humidity sensor; and determining the target capacitance for the drug dose based on the humidity measurement, wherein a relative permittivity sensor dielectric depends on humidity.

11. The method of claim 8, further comprising:
measuring a baseline capacitance prior to expelling the drug from the fluid chamber; and
calculating the target capacitance based on the baseline capacitance.

12. The method of claim 8, further comprising:
receiving at least one of a fluid chamber pressure from a pressure sensor and a stopper actuator power from a power sensor; and
in response to at least one of the fluid chamber pressure exceeding a threshold pressure and the stopper actuator power exceeding a threshold power, determining that the failure is an occlusion.

13. The method of claim 8, further comprising:
receiving at least one of a fluid chamber pressure from a pressure sensor and a stopper actuator power from a power sensor; and
in response to at least one of the fluid chamber pressure being lower than a threshold pressure and the stopper actuator power being lower than a threshold power, determining that the failure is a leakage.

14. The method of claim 8, further comprising:
prior to instructing the stopper actuator to expel the drug from the fluid chamber, performing a leakage detection procedure comprising:
obtaining a first capacitance measurement;
obtaining a second capacitance measurement a period of time after the first capacitance measurement; and
comparing the first capacitance measurement to the second capacitance measurement to determine whether the second capacitance measurement is within a threshold tolerance of the first capacitance measurement.

15. A drug delivery system comprising:
a syringe holder to hold a syringe containing a drug for delivery to a patient, the syringe comprising an air chamber, a fluid chamber, and a stopper separating the air chamber from the fluid chamber;
a stopper actuator couplable to the stopper;
a measurement circuit to measure a capacitance across a pair of electrodes arranged along either side of the container; and
a processor to:
receive a first measured capacitance from the measurement circuit;
determine, based on the first measured capacitance, a volume of the drug in the fluid chamber;
compare the volume of the drug in the fluid chamber to a target volume;
in response to the volume of the drug in the fluid chamber being greater than the target volume, instruct the stopper actuator to expel at least a portion of the drug from the fluid chamber;
after instructing the stopper actuator to expel the drug from the fluid chamber, receive a second measured capacitance from the measurement circuit; and
in response to a difference between the first measured capacitance and the second measured capacitance being less than an error threshold, determine that a failure has occurred.

16. The drug delivery system of claim 15, further comprising a voltage source to generate a voltage applied to the pair of electrodes to generate an electric field extending through at least a portion of the syringe.

17. The drug delivery system of claim 15, further comprising a memory to store data characterizing the drug, the processor further configured to determine the volume of the drug based on the data.

18. The drug delivery system of claim 15, further comprising a temperature sensor to measure a temperature, the processor further configured to determine the volume of the drug in the fluid chamber based on a temperature measurement received from the temperature sensor, wherein a relative permittivity of sensor dielectric depends on temperature.

19. The drug delivery system of claim 15, further comprising a humidity sensor to measure a humidity, the processor further configured to determine the volume of the drug in the fluid chamber based on a humidity measurement received from the humidity sensor, wherein a relative permittivity of sensor dielectric depends on humidity.

20. The drug delivery system of claim 15, further comprising a pressure sensor to measure a pressure in the fluid chamber, the processor further configured to detect at least one of an occlusion and a leakage based on a pressure measurement received from the pressure sensor.

21. The drug delivery system of claim 15, further comprising a power sensor to measure a power supplied to a motor of the stopper actuator, the processor further configured to detect at least one of an occlusion and a leakage based on a power measurement received from the power sensor.

22. A drug delivery system comprising:
a syringe holder to hold a syringe containing a drug for delivery to a patient, the syringe comprising an air chamber, a fluid chamber, and a stopper separating the air chamber from the fluid chamber;
a stopper actuator couplable to the stopper;
a measurement circuit to measure a capacitance across a pair of electrodes arranged along either side of the container; and
a processor to:
determine a target capacitance for a drug dose;
receive a first measured capacitance from the measurement circuit;
compare the first measured capacitance to the target capacitance;
in response to the first measured capacitance being greater than the target capacitance, instruct the stopper actuator to expel at least a portion of the drug from the fluid chamber;
after instructing the stopper actuator to expel the drug from the fluid chamber, receive a second measured capacitance from the measurement circuit; and
in response to a difference between the first measured capacitance and the second measured capacitance being less than an error threshold, determine that a failure has occurred.

23. The drug delivery system of claim 22, further comprising a voltage source to generate a voltage applied to the pair of electrodes to generate an electric field extending through at least a portion of the syringe.

24. The drug delivery system of claim 22, further comprising a memory to store data characterizing the drug, the processor further configured to determine the target capacitance for the drug dose based on the data.

25. The drug delivery system of claim 22, further comprising a temperature sensor to measure a temperature, the processor further configured to determine the target capacitance based on a temperature measurement received from the temperature sensor, wherein a relative permittivity of sensor dielectric depends on temperature.

26. The drug delivery system of claim 22, further comprising a humidity sensor to measure a humidity, the processor further configured to determine the target capacitance based on a humidity measurement received from the humidity sensor, wherein a relative permittivity of sensor dielectric depends on humidity.

27. The drug delivery system of claim 22, further comprising a pressure sensor to measure a pressure in the fluid chamber, the processor further configured to detect at least one of an occlusion and a leakage based on a pressure measurement received from the pressure sensor.

28. The drug delivery system of claim 22, further comprising a power sensor to measure a power supplied to a motor of the stopper actuator, the processor further configured to detect at least one of an occlusion and a leakage based on a power measurement received from the power sensor.

* * * * *